US010766781B2

(12) United States Patent
Parvulescu et al.

(10) Patent No.: US 10,766,781 B2
(45) Date of Patent: Sep. 8, 2020

(54) TIN-CONTAINING ZEOLITIC MATERIAL HAVING A BEA FRAMEWORK STRUCTURE

(71) Applicant: BASF SE, Ludwigshafen am Rhein (DE)

(72) Inventors: Andrei-Nicolae Parvulescu, Ruppertsberg (DE); Joaquim Henrique Teles, Waldsee (DE); Nicolas Vautravers, Mannheim (DE); Ulrich Müller, Neustadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/060,229

(22) PCT Filed: Dec. 7, 2016

(86) PCT No.: PCT/EP2016/080076
§ 371 (c)(1),
(2) Date: Jun. 7, 2018

(87) PCT Pub. No.: WO2017/097835
PCT Pub. Date: Jun. 15, 2017

(65) Prior Publication Data
US 2018/0362351 A1    Dec. 20, 2018

(30) Foreign Application Priority Data
Dec. 8, 2015    (EP) .................... 15198362

(51) Int. Cl.
| | | |
|---|---|---|
| *B01J 29/06* | (2006.01) | |
| *C01B 39/08* | (2006.01) | |
| *C01B 37/02* | (2006.01) | |
| *C01B 39/12* | (2006.01) | |
| *C01B 39/48* | (2006.01) | |
| *C07D 313/04* | (2006.01) | |
| *C07F 5/02* | (2006.01) | |
| *C07F 7/22* | (2006.01) | |
| *C07C 51/00* | (2006.01) | |
| *C07C 67/00* | (2006.01) | |
| *B01J 29/70* | (2006.01) | |
| *B01J 29/86* | (2006.01) | |
| *B01J 29/035* | (2006.01) | |
| *B01J 37/10* | (2006.01) | |
| *B01J 35/10* | (2006.01) | |
| *B01J 37/03* | (2006.01) | |
| *C07C 51/02* | (2006.01) | |

(52) U.S. Cl.
CPC ............ *C01B 39/08* (2013.01); *B01J 29/035* (2013.01); *B01J 29/7057* (2013.01); *B01J 29/86* (2013.01); *B01J 35/1019* (2013.01); *B01J 35/1023* (2013.01); *B01J 37/031* (2013.01); *B01J 37/036* (2013.01); *B01J 37/10* (2013.01); *C01B 37/02* (2013.01); *C01B 39/12* (2013.01); *C01B 39/48* (2013.01); *C07C 51/00* (2013.01); *C07C 51/02* (2013.01); *C07C 67/00* (2013.01); *C07D 313/04* (2013.01); *C07F 5/02* (2013.01); *C07F 7/22* (2013.01); *B01J 2229/183* (2013.01)

(58) Field of Classification Search
CPC ...... B01J 29/035; B01J 29/7057; B01J 29/86; B01J 2229/183; B01J 35/1019; B01J 35/1023; B01J 37/10; B01J 37/031; B01J 37/036; C01B 37/02; C01B 37/005; C01B 37/007; C01B 37/06; C01B 39/08; C01B 39/12; C01B 39/48; C07F 7/22; C07F 5/02; C07C 67/00; C07C 51/02
USPC .......... 502/60; 423/700, 701, 702, 704, 713, 423/718
See application file for complete search history.

(56) References Cited

U.S. PATENT DOCUMENTS

| | | | | |
|---|---|---|---|---|
| 5,324,702 A | * | 6/1994 | Yoo ..................... | B01J 37/06 502/204 |
| 6,197,717 B1 | * | 3/2001 | Alexander ............... | B01J 29/86 502/202 |
| 6,331,500 B1 | * | 12/2001 | Tsuji ....................... | B01J 20/18 423/701 |
| 9,108,190 B1 | | 8/2015 | Fan et al. | |
| 9,446,390 B2 | | 9/2016 | Parvulescu et al. | |
| 9,540,305 B2 | | 1/2017 | Parvulescu et al. | |

(Continued)

FOREIGN PATENT DOCUMENTS

| | | |
|---|---|---|
| CN | 104709920 A | 6/2015 |
| WO | WO-0181291 A2 | 11/2001 |

(Continued)

OTHER PUBLICATIONS

English Translation of International Preliminary Report On Patentability with Written Opinion for International Application No. PCT/EP2016/080076, dated Jun. 21, 2018.

(Continued)

*Primary Examiner* — Elizabeth D Wood
(74) *Attorney, Agent, or Firm* — Faegre Drinker Biddle & Reath LLP

(57) ABSTRACT

A process for preparing a tin-containing zeolitic material having framework type BEA, comprising providing an aqueous synthesis mixture comprising a boron source, a silicon source, and a BEA structure directing agent; subjecting the synthesis mixture provided in to hydrothermal pre-crystallization conditions; adding the tin source to the obtained mixture; subjecting the obtained aqueous synthesis mixture to hydrothermal crystallization conditions, obtaining a tin-containing zeolitic material having framework type BEA comprised in its mother liquor.

20 Claims, 12 Drawing Sheets

(56) References Cited

U.S. PATENT DOCUMENTS

Figure 1:
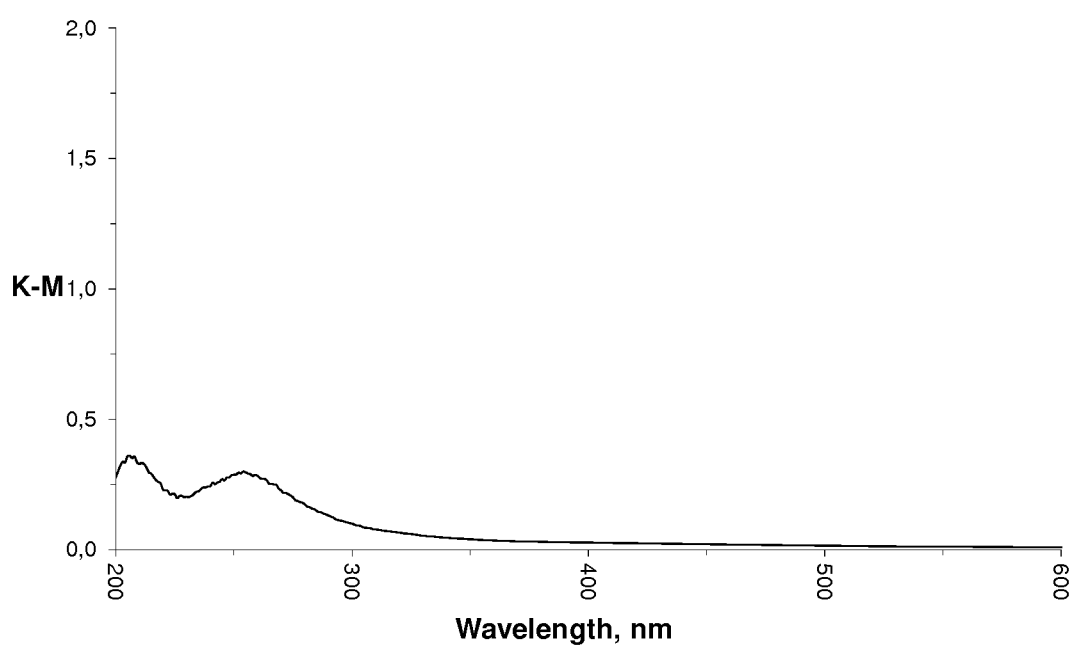

| | | | |
|---|---|---|---|
| 9,695,099 B2 | 7/2017 | Liu et al. | |
| 9,765,003 B2 | 9/2017 | Vautravers et al. | |
| 9,796,654 B2 | 10/2017 | Vautravers et al. | |
| 9,969,708 B2 | 5/2018 | Vautravers et al. | |
| 9,988,268 B2 | 6/2018 | Riedel et al. | |
| 2016/0067692 A1* | 3/2016 | Ouyang | B01J 29/86 |
| | | | 549/268 |
| 2016/0312149 A1 | 10/2016 | Vautravers et al. | |
| 2016/0318860 A1 | 11/2016 | Vautravers et al. | |
| 2016/0325228 A1 | 11/2016 | Feyen et al. | |
| 2017/0037296 A1 | 2/2017 | Kimura et al. | |
| 2017/0044421 A1 | 2/2017 | Parvulescu et al. | |
| 2017/0128916 A1 | 5/2017 | Lejkowski et al. | |
| 2017/0225959 A1 | 8/2017 | Maurer et al. | |
| 2017/0246620 A1 | 8/2017 | Parvulescu et al. | |
| 2017/0252729 A1* | 9/2017 | Schmidt | B01J 37/08 |
| 2017/0275076 A1 | 9/2017 | Edgington et al. | |
| 2017/0275225 A1 | 9/2017 | Riedel et al. | |
| 2017/0336030 A1 | 11/2017 | Weickert et al. | |
| 2017/0362532 A1 | 12/2017 | Pelzer et al. | |
| 2018/0022611 A1 | 1/2018 | Feyen et al. | |
| 2018/0036723 A1 | 2/2018 | Riedel et al. | |
| 2018/0134570 A1 | 5/2018 | Maurer et al. | |
| 2018/0170850 A1 | 6/2018 | Vautravers et al. | |
| 2018/0178191 A1 | 6/2018 | Schwab et al. | |
| 2018/0186648 A1 | 7/2018 | Feyen et al. | |
| 2018/0208532 A1 | 7/2018 | Parvulescu et al. | |
| 2018/0208533 A1 | 7/2018 | Rudenauer et al. | |
| 2018/0208745 A1 | 7/2018 | Vautravers et al. | |
| 2018/0215694 A1 | 8/2018 | Riedel et al. | |
| 2018/0215724 A1 | 8/2018 | Gordillo et al. | |
| 2019/0168197 A1* | 6/2019 | Corma Canos | B01J 20/18 |

FOREIGN PATENT DOCUMENTS

| | | |
|---|---|---|
| WO | WO-2015067654 A1 | 5/2015 |
| WO | WO-2015123530 A1 | 8/2015 |
| WO | WO-2015123531 A1 | 8/2015 |
| WO | WO-2015169939 A1 | 11/2015 |
| WO | WO-2015197699 A1 | 12/2015 |
| WO | WO-2016024201 A1 | 2/2016 |
| WO | WO-2016074918 A1 | 5/2016 |
| WO | WO-2016075100 A1 | 5/2016 |
| WO | WO-2016075129 A1 | 5/2016 |
| WO | WO-2016135133 A1 | 9/2016 |
| WO | WO-2016180809 A1 | 11/2016 |
| WO | WO-2017060440 A1 | 4/2017 |
| WO | WO-2017085049 A1 | 5/2017 |
| WO | WO-2017089344 A1 | 6/2017 |

OTHER PUBLICATIONS

Tolborg, S., et al., "Incorporation of tin affects crystallization, morphology, and crystal composition of Sn-Beta", Journal of Materials Chemistry A, 2014, pp. 20252-20262.

Dijkmans, J., et al., "Post-synthesis Snβ: An exploration of synthesis parameters and catalysis", Journal of Catalysis, vol. 330, (2015), pp. 545-557.

Hammond, C., et al., "Simple and Scalable Preparation of Highly Active Lewis Acidic Sn-β", Angewandte Chemie International Edition, vol. 51, No. 47, (2012), pp. 11736-11739.

International Search Report for PCT/EP2016/080015 dated Jan. 24, 2017.

International Search Report for PCT/EP2016/080076 dated Jan. 24, 2017.

Kang, Z., et al., "Preparation and Characterization of Sn-β Zeolites by a Two-Step Postsynthesis Method and Their Catalytic Performance for Baeyer-Villiger Oxidation of Cyclohexanone", Chinese Journal of Catalysis, vol. 33, No. 5, (2012), pp. 898-904.

Liu, M., et al., "Facile preparation of Sn-β zeolites by post-synthesis (isomorphous substitution) method for isomerization of glucose to fructose", Chinese Journal of Catalysis, vol. 35, No. 5, (2014), pp. 723-732.

Written Opinion of the International Searching Authority for PCT/EP2016/080015 dated Jan. 24, 2017.

Written Opinion of the International Searching Authority for PCT/EP2016/080076 dated Jan. 24, 2017.

U.S. Appl. No. 15/514,902, filed Mar. 28, 2017, BASF SE.
U.S. Appl. No. 15/521,924, filed Apr. 26, 2017.
U.S. Appl. No. 15/537,128, filed Jun. 16, 2017, Vautravers et al.
U.S. Appl. No. 15/752,991, filed Feb. 15, 2018.
U.S. Appl. No. 15/766,425, filed Apr. 6, 2018, Thrun et al.
U.S. Appl. No. 15/777,931, filed May 22, 2018.
U.S. Appl. No. 16/060,260, filed Jun. 7, 2018.
U.S. Appl. No. 15/779,314, filed Jul. 30, 2018.

* cited by examiner

TIN-CONTAINING ZEOLITIC MATERIAL HAVING A BEA FRAMEWORK STRUCTURE

CROSS-REFERENCE TO RELATED APPLICATIONS

This application is a national stage application (under 35 U.S.C. § 371) of PCT/EP2016/080076, filed Dec. 7, 2016, which claims benefit of European Application No. 15198362.4, filed Dec. 8, 2015, both of which are incorporated herein by reference in their entirety.

The present invention relates to a process for preparing a tin-containing zeolitic material having framework type BEA. According to this process, a tin-containing zeolitic material having framework type BEA is obtained which contains boron in its framework. This tin- and boron-containing zeolitic material having framework type BEA can be subjected to a suitable deboronation stage. The present invention also relates to the respectively obtained zeolitic material having framework type BEA, and to its use.

Zeolites having the framework type BEA (zeolite beta) and further comprising tin have shown promising results if used as catalytically active materials in certain applications such as Baeyer-Villiger-type oxidation reactions, isomerization reactions, and the like.

Tin containing zeolites having BEA framework structure are usually prepared by incorporation of tin into the zeolitic framework zeolites having BEA framework by hydrothermally treating a zeolitic material having vacant tetrahedral framework sites in the presence of a suitable tin-ion source. However, regarding this hydrothermal incorporation of tin, disadvantages have to be taken into account such as long synthesis time periods, the necessity to employ crystallization auxiliaries such as HF or cost intensive templating agents.

With regard to a direct hydrothermal synthesis of tin containing zeolites having BEA framework structure, fluoride based systems are known. For example, U.S. Pat. No. 9,108,190 describes a direct synthesis of such zeolites by various fluoride based systems and, additionally, a fluoride-free route through a complicated dry-gel conversion method by using highly alkaline media which, in particular in industrial-scale process, should be avoided. J. Mater. Chem. A 2 (2014) pp 20252-20262 gives an overview of hydrothermal and fluoride-based synthesis methods for preparing tin containing zeolites having BEA framework structure.

Therefore, it was an object of the invention to provide a novel and advantageous process for preparing a tin containing zeolites having BEA framework structure which avoids drawbacks of the known processes.

Surprisingly, it was found that this object can be achieved by hydrothermally synthesizing a tin containing zeolites having BEA framework structure starting from a synthesis mixture which contains both a tin source and a boron source, from which synthesis mixture, after hydrothermal synthesis, a tin containing zeolites having BEA framework structure is obtained which can be subjected to a suitable deboronation.

In particular, it was found that this object can be achieved by precrystallizing a precursor based on a synthesis mixture comprising a boron source, and subjecting this precursor to hydrothermally synthesis in the presence of a tin source, obtaining, after hydrothermal synthesis, a tin containing zeolites having BEA framework structure which can be subjected to a suitable deboronation.

Therefore, the present invention relates to a process for preparing a tin-containing zeolitic material having framework type BEA, comprising (i) providing an aqueous synthesis mixture comprising sources of tin, boron and silicon, and a framework type BEA structure directing agent;
(ii) subjecting the aqueous synthesis mixture provided in (i) to hydrothermal crystallization conditions, obtaining a tin-containing zeolitic material having framework type BEA comprised in its mother liquor.

With regard to suitable sources of tin, boron and silicon, and a framework type BEA structure directing agent, reference is made to the respective discussion below. In particular, it is possible that the process comprises (i) providing an aqueous synthesis mixture comprising a tin source, a boron source and a silicon source, and a framework type BEA structure directing agent;
(ii) subjecting the aqueous synthesis mixture provided in (i) to hydrothermal crystallization conditions, obtaining a tin-containing zeolitic material having framework type BEA comprised in its mother liquor.

Preferably, step (i) of the process comprises a precrystallization step wherein a precursor is prepared based on a synthesis mixture which comprises a boron source, a silicon source, and a BEA structure directing agent, and which does not comprise a tin source. In a further step, based on this precursor and a suitable tin source, a tin-containing zeolitic material having framework type BEA is hydrothermally synthesized. In terms of the process described above, the said precursor would represent a suitable source of boron and silicon and a framework type BEA structure directing agent.

Therefore, the present invention also relates to a process, preferably a process as defined above, comprising (i.1) providing an aqueous synthesis mixture comprising a boron source, a silicon source, and a framework type BEA structure directing agent;
(i.2) subjecting the synthesis mixture provided in (i) to hydrothermal pre-crystallization conditions;
(i.3) adding the tin source to the mixture obtained from (i.2);
(ii) subjecting the aqueous synthesis mixture obtained from (i.3) to hydrothermal crystallization conditions, obtaining a tin-containing zeolitic material having framework type BEA comprised in its mother liquor.

Further, the present invention also relates to a process, preferably a process as defined above, comprising (i.1) providing an aqueous synthesis mixture comprising a boron source, a silicon source, and a framework type BEA structure directing agent, wherein this aqueous synthesis mixture does not comprise a tin source;
(i.2) subjecting the synthesis mixture provided in (i) to hydrothermal pre-crystallization conditions;
(i.3) adding the tin source to the mixture obtained from (i.2);
(ii) subjecting the aqueous synthesis mixture obtained from (i.3) to hydrothermal crystallization conditions, obtaining a tin-containing zeolitic material having framework type BEA comprised in its mother liquor.

With regard to the composition of the aqueous synthesis mixture provided in (i.1), no specific restrictions exist. Generally, it is possible that in addition to the water, the boron source, the silicon source, and the framework type BEA structure directing agent, the aqueous synthesis mixture comprises one or more further components. Preferably, at least 99 weight-%, preferably at least 99.5 weight-%, more preferably at least 99.9 weight-% of the aqueous synthesis mixture provided in (i.1) consist of the water, the boron source, the silicon source, and the framework type BEA structure directing agent.

In the context of the present invention, if the term "water" is used, this term preferably describes water having a conductivity of at most 50 microSiemens/cm.

The boron source, the silicon source, and the framework type BEA structure directing agent can be admixed in (i.1) in any suitably order. It may be preferred, for example, to admix the framework type BEA structure directing and the boron source, followed by adding the silicon source. Preferably, preparing the mixture comprises agitating, preferably stirring.

Preferably, the hydrothermal pre-crystallization according to (i.2) is carried out in an autoclave. The mixture provided in (i.1) can be prepared in this autoclave, or can be prepared in a suitable vessel and, after its preparation, be filled in the autoclave.

Preferably, the hydrothermal pre-crystallization conditions according to (i.2) comprise a hydrothermal pre-crystallization temperature in the range of from 100 to 200° C., preferably in the range of from 110 to 190° C., more preferably in the range of from 120 to 180° C. Preferred ranges are from 120 to 140° C. or from 130 to 150° C. or from 140 to 160° C. or from 150 to 170° C. or from 160 to 180° C.

Preferably, the hydrothermal pre-crystallization conditions according to (i.2) comprise a pre-crystallization under autogenous pressure, preferably an absolute hydrothermal pre-crystallization pressure in the range of from 1 to 30 bar.

The hydrothermal pre-crystallization time according to (i.2) may depend on the scale of the process. Typically, the hydrothermal pre-crystallization conditions according to (i.2) comprise a hydrothermal pre-crystallization time in the range of from 6 to 72 h, preferably in the range of from 9 to 60 h, more preferably in the range of from 12 to 48 h.

Preferably, the pre-crystallization according to (i.1.2) is conducted by means of agitation, preferably by rotating the autoclave or tumbling the autoclave and/or stirring the synthesis mixture in the autoclave, more preferably by stirring the mixture in the autoclave.

Generally, it is conceivable that the aqueous synthesis mixture subjected to hydrothermal pre-crystallization conditions according to (i.2) comprises a suitable seeding material. Preferably, the hydrothermal pre-crystallization conditions according to (i.2) do not comprise seeding.

With regard to the boron source, no specific restrictions exist. Generally, the boron source may be provided as $B_2O_3$ as such and/or as a compound which comprises $B_2O_3$ as a chemical moiety and/or as a compound which, partly or entirely, is chemically transformed to $B_2O_3$ during the process. Preferably, free boric acid and/or borates and/or boric esters, such as, for example, triethyl borate, trimethyl borate, 2,4,6-trimethoxy boroxine, or 2,4,6-triethoxy boroxine, are used as the boron source. More preferably, the boron source is one or more of boric acid, borates, boron halides, and boron oxide ($B_2O_3$). More preferably, the boron source comprises, more preferably is, boric acid.

With regard to the silicon source, no specific restrictions exist. Generally, the silicon source is provided as $SiO_2$ as such and/or as a compound which comprises $SiO_2$ as a chemical moiety and/or as a compound which, partly or entirely, is chemically transformed to $SiO_2$ during the process wherein generally, all types of silica and silicates, preferably fumed silica, silica hydrosols, reactive amorphous solid silica, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds can be used. Preferably, the silicon source is one or more of fumed silica and colloidal silica. More preferably, the silicon source comprises, more preferably is, colloidal silica. More preferably, the silicon source comprises, more preferably is, ammonia-stabilized colloidal silica.

According to the present invention, the framework type BEA structure directing agent can be any suitable compound. Suitable template compounds include, for example, tetraethylammonium hydroxide. Preferably, the framework type BEA structure directing agent comprises, more preferably is, tetraethylammonium hydroxide.

In the aqueous synthesis mixture provided in (i), preferably in (i.1), the weight ratio of boron relative to silicon is preferably in the range of from 0.4:1 to 2.0:1, more preferably in the range of from 0.6:1 to 1.7:1, more preferably in the range of from 0.9:1 to 1.4:1. Preferred ranges are from 0.9:1 to 1.1:1 or from 1.0:1 to 1.2:1 or from 1.1:1 to 1.3:1 or from 1.2:1 to 1.4:1.

Further, in the aqueous synthesis mixture provided in (i), preferably in (i.1), the weight ratio of the framework type BEA structure directing agent relative to silicon is in the range of from 0.10:1 to 0.30:1, preferably in the range of from 0.15:1 to 0.27:1, more preferably in the range of from 0.20:1 to 0.24:1. Preferred ranges are from 0.20:1 to 0.22:1 or from 0.21:1 to 0.23:1 or from 0.22:1 to 0.24:1.

Preferably, after the pre-crystallization step according to (i.2) and before (i.3), the respectively obtained pre-crystallizate is cooled, preferably in the autoclave, preferably to a temperature in the range of from 0 to 80° C., more preferably in the range of from 25 to 50° C.

After the pre-crystallization according to (i.2), the tin source is added to the pre-crystallizate obtained from (i.2). For this purpose, the pre-crystallizate can be removed from the vessel in which the pre-crystallization had been carried out, and be admixed with the tin source wherein the resulting mixture is either passed in the vessel in which the pre-crystallization had been carried out or passed in another suitable vessel, preferably another autoclave. Preferably, the pre-crystallizate is not removed from the vessel in which the pre-crystallization had been carried out, and the tin source is added to the pre-crystallizate in said vessel. It is conceivable that by using a suitable set-up, the tin source is added to the pre-crystallizate in said vessel which is still under the autogenous pressure under which the pre-crystallization had been carried out, preferably under the autogenous pressure in said vessel after cooling as described above. Preferably, the tin source is added under agitation, more preferably under stirring; in this case, it is conveivable possible that prior to adding the tin source, the pre-crystallizate is not cooled but kept at essentially the same temperature at which the pre-crystallization was carried out.

With regard to the tin source, no specific restrictions exist. Preferably, the tin source is one or more of tin(II) alkoxides, tin(IV) alkoxides, tin(II) salts of organic acids, tin(IV) salts of organic acids, tin(II) salts of inorganic acids, tin(IV) salts of inorganic acids. More preferably, the tin source is one or more of $SnCl_4$, Sn(IV)-acetate, Sn(IV)-tert-butoxide, $SnBr_4$, $SnF_4$, Sn(IV)-bisacetylacetonate dichloride, Sn(IV)-bisacetylacetonate dibromide, Sn(II)-acetate, Sn(II)-acetylacetonate, Sn(II)-citrate, $SnCl_2$, $SnF_2$, $SnI_2$, $SnSO_4$. More preferably, the tin source is one or more of Sn(II)-acetate or Sn(IV)-tert-butoxide.

Preferably, in the aqueous synthesis mixture provided in (i), preferably in the mixture obtained from (i.3), the weight ratio of tin relative to silicon is in the range of from 0.005:1 to 0.1:1, preferably in the range of from 0.01:1 to 0.06:1, more preferably in the range of from 0.02:1 to 0.05:1. Preferred ranges are from 0.02:1 to 0.04:1 or from 0.03:1 to 0.05:1.

Preferably, the aqueous synthesis mixture subjected to hydrothermal crystallization conditions in (ii) comprises at most 0.1 weight-%, preferably at most 0.05 weight-% aluminum, calculated as elemental Al and based on the total weight of the aqueous synthesis mixture. Thus, it is preferred that the aqueous synthesis mixture provided in (i.1) and subjected to pre-crystallization conditions in (i.2) and the aqueous synthesis mixture obtained from (i.3) comprise at most 0.1 weight-%, preferably at most 0.05 weight-% aluminum, calculated as elemental Al and based on the total weight of the respective aqueous synthesis mixture. If at all, the aluminum comprised in said mixtures is present as impurity in the silicon source and/or the boron source and/or the framework type BEA structure directing agent and/or the tin source and/or the water. In particular, no aluminum source is deliberately employed in the respective aqueous synthesis mixtures.

Preferably, at least 99 weight-%, more preferably at least 99.5 weight-%, more preferably at least 99.9 weight-% of the aqueous synthesis mixture subjected to hydrothermal crystallization conditions in (ii) consist of the mixture obtained from (i.3) and the tin source. Preferably, the aqueous synthesis mixture subjected to hydrothermal crystallization conditions in (ii) has a fluoride content of at most 0.1 weight-%, preferably of at most 0.05 weight-%, calculated as elemental F and based on the total weight of the aqueous synthesis mixture. Preferably, the aqueous synthesis mixture subjected to hydrothermal crystallization conditions in (ii) has total content of alkali metal and alkaline earth metal of at most 0.1 weight-%, preferably of at most 0.05 weight-% calculated as elemental alkali metal and alkaline earth metal and based on the total weight of the aqueous synthesis mixture. Preferably, the aqueous synthesis mixture subjected to hydrothermal crystallization conditions in (ii) has a hydrogen peroxide content of at most 0.01 weight-%, preferably of at most 0.001 weight-%, more preferably of 0 weight-%, based on the total weight of the aqueous synthesis mixture.

Preferably, the hydrothermal crystallization conditions according to (ii) comprise a hydrothermal pre-crystallization temperature in the range of from 100 to 200° C., preferably in the range of from 110 to 190° C., more preferably in the range of from 120 to 180° C. Preferred ranges are from 120 to 140° C. or from 130 to 150° C. or from 140 to 160° C. or from 150 to 170° C. or from 160 to 180° C.

Preferably, the hydrothermal crystallization conditions according to (ii) comprise a pre-crystallization under autogenous pressure, preferably an absolute hydrothermal pre-crystallization pressure in the range of from 1 to 30 bar.

The hydrothermal crystallization time according to (ii) may depend on the scale of the process. Typically, the hydrothermal crystallization conditions according to (ii) comprise a hydrothermal crystallization time in the range of from 6 to 240 h, preferably in the range of from 9 to 180 h, more preferably in the range of from 12 to 120 h.

Preferably, the crystallization according to (ii) is conducted by means of agitation, preferably by rotating the autoclave or tumbling the autoclave and/or stirring the synthesis mixture in the autoclave, more preferably by stirring the mixture in the autoclave.

Generally, it is conceivable that the aqueous synthesis mixture subjected to hydrothermal pre-crystallization conditions according to (ii) comprises a suitable seeding material. Preferably, the hydrothermal crystallization conditions according to (ii) do not comprise seeding.

Preferably, after the crystallization step according to (ii), the respectively obtained mother liquor comprising a tin-containing zeolitic material having framework type BEA is cooled, preferably in the autoclave, preferably to a temperature in the range of from 0 to 80° C., more preferably in the range of from 25 to 50° C. Further preferably, the autoclave is subjected to a suitable pressure release.

After step (ii), the tin-containing zeolitic material having framework type BEA is preferably separated from its mother liquor. No specific restrictions exist with regard to a suitable separation method, and every solid-liquid separation technique is conceivable. Preferred separation methods include, but are not restricted to, filtration such as suction or pressure filtration, centrifugation, rapid drying such as spray-drying or spray-granulation.

For the purpose of the separation according to (iii), in particular filtration, the pH of the mother liquor obtained from (ii) containing the crystallized zeolitic material is adjusted to a value in the range of from 6 to 8.5, preferably from 6.5 to 8, more preferably from 7 to 8, preferably by adding an acid to the mother liquor, preferably under stirring, wherein the adding of the acid is preferably carried out at a temperature of the mother liquor in the range of from 20 to 70° C., more preferably from 30 to 65° C., more preferably from 40 to 60° C. The acid is preferably an inorganic acid, preferably in the form of an aqueous solution containing the inorganic acid, wherein the inorganic acid is preferably selected from the group consisting of phosphoric acid, sulphuric acid, hydrochloric acid, nitric acid, and a mixture of two or more thereof, and wherein the inorganic acid is more preferably nitric acid.

Preferably, the separating according to (iii) comprises washing the tin-containing zeolitic material having framework type BEA with a washing agent. Any conceivable washing agent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, with water being particularly preferred as the washing agent.

The crystallized zeolitic material is preferably separated in (iii) from the suspension obtained from (ii) by filtration to obtain a filter cake which is preferably subjected to washing, preferably with water. If washing is applied, it is preferred to continue the washing process until the washing water has a conductivity of at most 1,000 microSiemens/cm, more preferably of at most 850 microSiemens/cm, more preferably of at most 700 microSiemens/cm.

Therefore, it is preferred that the separating according to (iii) comprises
(iii.1) preparing an aqueous suspension comprising the mother liquor and the tin-containing zeolitic material having framework type BEA and having a pH in the range of from 6 to 8.5, preferably in the range of from 7 to 8;
(iii.2) separating at least a portion of the liquid phase from the aqueous suspension;

(iii.3) washing the tin-containing zeolitic material having framework type BEA obtained from (iii.2) with a washing agent, preferably water.

After the separation, and preferably after washing, the tin-containing zeolitic material having framework type BEA is preferably subjected to drying conditions according to a step (iv). Optionally, prior to drying according to (iv), the zeolitic material can be subjected to pre-drying, for example by subjecting the zeolitic material to a suitable gas stream such as air, lean air, or technical nitrogen, for a time preferably in the range of from 4 to 10 h, more preferably from 5 to 8 h.

As mentioned, the optionally pre-dried zeolitic material is preferably dried. Suitable drying methods include, but are not restricted to, conventional drying in an oven, either as batch or continuous drying process, rapid-drying such as spray-drying or spray-granulation, flash drying, or microwave drying. Preferably, drying is carried out at a temperature in the range of from 60 to 200° C., more preferably from 80 to 190° C., more preferably from 100 to 180° C. in a suitable atmosphere such as technical nitrogen, air, or lean air. Preferred temperature ranges are from 100 to 140° C. or from 120 to 160° C. or from 140 to 180° C. Preferably, the drying conditions according to (iv) comprise a drying atmosphere comprising oxygen, preferably air or lean air, more preferably air, or comprise a drying atmosphere comprising nitrogen, wherein more preferably, the atmosphere is technical nitrogen.

If the drying is accomplished by rapid-drying, a preferably aqueous suspension is preferably prepared from the optionally pre-dried zeolitic material. If rapid-drying is carried out, it is conceivable to subject the mother liquor obtained from (ii) containing the zeolitic material, optionally after concentration and/or pH adjustment as described above, directly to rapid-drying. Further, it is conceivable to subject the separated and washed zeolitic material to rapid-drying, optionally after suitable re-suspending of the washed and optionally pre-dried zeolitic material wherein aqueous suspensions are preferably prepared having preferred solids content range of from 2 to 35 weight-%, preferably from 5 to 25 weight-%, more preferably from 10 to 20 weight-%, based on the total weight of the suspension.

The preferably washed and preferably dried zeolitic material is preferably subjected in a further step (v) to calcination conditions. Preferably, during calcination, the framework type BEA structure directing agent is at least partially, more preferably essentially removed from the framework structure. The calcination generally involves the heating of the zeolitic material to a temperature of at least 350° C., preferably to a temperature in the range of from 400 to 700° C., more preferably from 420 to 680° C., more preferably from 450 to 650° C. in a suitable atmosphere such as technical nitrogen, air, or lean air. Preferred temperature ranges are from 450 to 500° C. or from 500 to 550° C. or from 550 to 600° C. or from 600 to 650° C. Preferably, the calcination conditions according to (v) comprise a calcination atmosphere comprising oxygen, preferably air or lean air, more preferably air.

The respectively obtained zeolitic material having framework type BEA comprises, preferably essentially consists of, tin, boron, silicon, oxygen, and hydrogen. Therefore, in particular, the present invention also relates to a process for preparing a tin- and boron-containing zeolitic material having framework type BEA, the process comprising (i) providing an aqueous synthesis mixture comprising sources of tin, boron and silicon, and a framework type BEA structure directing agent; said step (i) preferably comprising
  (i.1) providing an aqueous synthesis mixture comprising a boron source, a silicon source, and a framework type BEA structure directing agent, wherein the aqueous synthesis mixture does not comprise a tin source;
  (i.2) subjecting the synthesis mixture provided in (i) to hydrothermal pre-crystallization conditions;
  (i.3) adding the tin source to the mixture obtained from (i.2);
(ii) subjecting the aqueous synthesis mixture obtained from (i.3) to hydrothermal crystallization conditions, obtaining a tin- and boron-containing zeolitic material having framework type BEA comprised in its mother liquor;
(iii) separating the tin- and boron-containing zeolitic material having framework type BEA from its mother liquor, said step (iii) preferably comprising
  (iii.1) preparing an aqueous suspension comprising the mother liquor and the tin- and boron-containing zeolitic material having framework type BEA and having a pH in the range of from 6 to 8.5, preferably in the range of from 7 to 8;
  (iii.2) separating at least a portion of the liquid phase from the aqueous suspension;
  (iii.3) washing the tin- and boron-containing zeolitic material having framework type BEA obtained from (iii.2) with a washing agent, preferably water;
(iv) subjecting the tin- and boron-containing zeolitic material having framework type BEA obtained from (iii.3) to drying conditions;
(v) subjecting the tin- and boron-containing zeolitic material having framework type BEA to calcination conditions.

Accordingly, the present invention also relates to a tin- and boron-containing zeolitic material having framework type BEA which is obtainable or obtained by a process as described above.

Further, the present invention relates to a tin- and boron-containing zeolitic material having framework type BEA, having a tin content in the range of from 0.5 to 10 weight-%, calculated as elemental tin and based on the total weight of the tin- and boron-containing zeolitic material having framework type BEA, and having a boron content in the range of from 0.5 to 9 weight-%, calculated as elemental boron and based on the total weight of the tin- and boron-containing zeolitic material having framework type BEA, wherein said tin- and boron-containing zeolitic material having framework type BEA is preferably in its calcined state. More preferably, the tin- and boron-containing zeolitic material having framework type BEA has a tin content in the range of from 0.75 to 9 weight-%, more preferably in the range of from 1 to 8 weight-%, more preferably in the range of from 1.5 to 7.5 weight-%. More preferably, the tin- and boron-containing zeolitic material having framework type BEA has a boron content in the range of from 0.75 to 8 weight-%, preferably in the range of from 1 to 7 weight-%. Preferably, at least 99 weight-%, more preferably at least 99.5 weight-%, more preferably at least 99.9 weight-% of the zeolitic framework of the tin- and boron-containing zeolitic material having framework type BEA consist of Sn, B, Si, O, and H.

Preferably, said tin- and boron-containing zeolitic material having framework type BEA has a BET specific surface of at least 400 m$^2$/g, more preferably in the range of from 400 to 600 m$^2$/g, more preferably in the range of from 450 to 550 m$^2$/g, as determined according to DIN 66131.

Preferably, said tin- and boron-containing zeolitic material having framework type BEA has a crystallinity of at least 50%, preferably of at least 55%, more preferably in the range of from 55 to 85%, more preferably in the range of from 60 to 85%, more preferably in the range of from 65 to 85%, as determined according to XRD, preferably as defined in Reference Example 5 herein.

Preferably, said tin- and boron-containing zeolitic material having framework type BEA has a micropore volume in the range of from 0.10 to 0.25 cm$^3$/g, as determined according to DIN 66135.

Preferably, said tin- and boron-containing zeolitic material having framework type BEA has a mean crystal size of at most 100 nm, preferably in the range of from 5 to 100 nm, as determined according to SEM, preferably as defined in Reference Example 1 herein.

Preferably, said tin- and boron-containing zeolitic material having framework type BEA has an absorption band with a maximum in the range of from 200 to 220 nm and optionally a further absorption band with a maximum in the range of from 230 to 300 nm, as determined according to UV-VIS, preferably as defined in Reference Example 2 herein.

Preferably, said tin- and boron-containing zeolitic material having framework type BEA exhibits an FT-IR spectrum, preferably determined as defined in Reference Example 3 herein, wherein the ratio of the absorption maximum of a first band with a maximum in the range of from 3700 to 3750 cm$^{-1}$ relative to the absorption maximum of a second band with a maximum in the range of from 3550 to 3699 cm$^{-1}$ is in the range of from 0.5 to 2.0, preferably in the range of from 0.7 to 1.5.

Preferably, said tin- and boron-containing zeolitic material having framework type BEA exhibits a water uptake of at least 10 weight-%, preferably in the range from 10 to 35 weight-%, more preferably in the range from 15 to 35 weight-%, more preferably in the range from 20 to 35 weight-%, as determined via water adsorption-desorption isotherms, preferably as defined in Reference Example 4 herein.

Preferably, said tin- and boron-containing zeolitic material having framework type BEA is characterized by an XRD spectrum comprising peaks at 2 theta diffraction angles of (8.0±0.1)°, (22.0±0.1)°, (23.0±0.1)°, (25.9±0.1)°, (27.3±0.1)°.

Generally, the tin- and boron-containing zeolitic material having framework type BEA can be used for any suitable purpose. Preferably, it is used as a catalytically active material, preferably as a bifunctional catalytically active material, more preferably as a bifunctional catalytically active material in a reaction for which a catalytically active acid function is combined with a catalytically active redox function of the catalytically active material. Examples of such reactions include, but are not limited to, epoxidation and ring-opening reactions or epoxidation and etherification reactions or ring-opening and etherification reactions.

The process of the present invention is not only suitable for preparing then above-described tin- and boron-containing zeolitic material having framework type BEA. Additionally, the process of the invention provides an advantageous process for preparing a tin-containing zeolitic material having framework type BEA which is essentially free of boron. According to the present invention, this is easily achieved by a deboronation of the tin- and boron-containing zeolitic material having framework type BEA, preferably the washed tin- and boron-containing zeolitic material having framework type BEA, more preferably the washed and dried tin- and boron-containing zeolitic material having framework type BEA, more preferably the washed, dried and calcined tin- and boron-containing zeolitic material having framework type BEA.

Therefore, the present also relates to a process as described above, further comprising (vi) subjecting the tin-containing zeolitic material having framework type BEA to deboronation, obtaining a deboronated tin-containing zeolitic material.

No specific restrictions exist how said deboronation is carried, provided that said deboronated tin-containing zeolitic material is obtained.

According to a first embodiment, it is preferred that said deboronation comprises treating the tin- and boron-containing zeolitic material having framework type BEA with an acid, preferably followed by washing step. Therefore, the present invention also relates to the process as described above, further comprising (vi.1) treating the tin-containing zeolitic material having framework type BEA with an acid;

(vi.2) washing the acid-treated tin-containing zeolitic material having framework type BEA with a washing agent, preferably water.

According to a second embodiment, it is preferred that said deboronation comprises treating the tin- and boron-containing zeolitic material having framework type BEA with water which does not contain an acid, optionally followed by washing step. Therefore, the present invention also relates to the process as described above, further comprising (vi.1) treating the tin-containing zeolitic material having framework type BEA with water which does not contain an acid;

(vi.2) optionally washing the water-treated tin-containing zeolitic material having framework type BEA with a washing agent, preferably water.

With regard to said acid, no specific restrictions exist. Suitable acids include inorganic acids and organic acids, preferably having a pKa of at most 5. Inorganic acids are preferred, with sulfuric acid, hydrochloric acid, and nitric acid being more preferred. More preferably, the acid according to (vi.1) comprises, more preferably consists of, nitric acid.

Preferably, the treating according to (vi.1) is carried out in an aqueous mixture comprising the tin-containing zeolitic material having framework type BEA. Therefore, in case the dried, preferably the the dried and calcined tin- and boron-containing zeolitic material having framework type BEA described above is used as starting material for the deboronation, it is preferred that an aqueous suspension of the tin- and boron-containing zeolitic material having framework type BEA is prepared and subjected to (vi.1).

Preferably, said aqueous mixture comprising the tin-containing zeolitic material having framework type BEA is treated according to (vi.1) at a temperature of the mixture in the range of from 60 to 100° C., preferably in the range of from 80 to 100° C., more preferably in the range of from 90 to 100° C. Preferably, the treating according to (vi.1) is carried out under reflux.

After step (vi.1), the tin-containing zeolitic material having framework type BEA is preferably separated from the liquid portion of the suspension. No specific restrictions exist with regard to a suitable separation method, and every solid-liquid separation technique is conceivable. Preferred separation methods include, but are not restricted to, filtration such as suction or pressure filtration, centrifugation, rapid drying such as spray-drying or spray-granulation.

Preferably, after said separation, the tin-containing zeolitic material having framework type BEA is washed with a washing agent, in particular if the treatment according to (vi.1) comprises a treatment with an acid. Any conceivable washing agent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, with water being particularly preferred as the washing agent. It is preferred to continue the washing process until the washing water has a conductivity of at most 1,000 microSiemens/cm, more preferably of at most 850 microSiemens/cm, more preferably of at most 700 microSiemens/cm.

After the preferred separation and after the washing, the tin-containing zeolitic material having framework type BEA is preferably subjected to drying conditions according to a step (vii). Optionally, prior to drying according to (vii), the zeolitic material can be subjected to pre-drying, for example by subjecting the zeolitic material to a suitable gas stream such as air, lean air, or technical nitrogen, for a time preferably in the range of from 4 to 10 h, more preferably from 5 to 8 h.

As mentioned, the optionally pre-dried zeolitic material is preferably dried. Suitable drying methods include, but are not restricted to, conventional drying in an oven, either as batch or continuous drying process, rapid-drying such as spray-drying or spray-granulation, flash drying, or microwave drying. Preferably, drying is carried out at a temperature in the range of from 60 to 200° C., more preferably from 80 to 190° C., more preferably from 100 to 180° C. in a suitable atmosphere such as technical nitrogen, air, or lean air. Preferred temperature ranges are from 100 to 140° C. or from 120 to 160° C. or from 140 to 180° C. Preferably, the drying conditions according to (vii) comprise a drying atmosphere comprising comprising nitrogen, preferably nitrogen, air, or lean air, or comprise a drying atmosphere comprising nitrogen, wherein more preferably, the atmosphere is technical nitrogen.

If the drying is accomplished by rapid-drying, a preferably aqueous suspension is preferably prepared from the optionally pre-dried zeolitic material. If rapid-drying is carried out, it is conceivable to subject the mother liquor obtained from (ii) containing the zeolitic material, optionally after concentration and/or pH adjustment as described above, directly to rapid-drying. Further, it is conceivable to subject the separated and washed zeolitic material to rapid-drying, optionally after suitable re-suspending of the washed and optionally pre-dried zeolitic material wherein aqueous suspensions are preferably prepared having preferred solids content range of from 2 to 35 weight-%, preferably from 5 to 25 weight-%, more preferably from 10 to 20 weight-%, based on the total weight of the suspension.

The preferably washed and preferably dried zeolitic material is preferably subjected in a further step (viii) to calcination conditions. The calcination generally involves the heating of the zeolitic material to a temperature of at least 350° C., preferably to a temperature in the range of from 400 to 700° C., more preferably from 420 to 680° C., more preferably from 450 to 650° C. in a suitable atmosphere such as technical nitrogen, air, or lean air. Preferred temperature ranges are from 450 to 500° C. or from 500 to 550° C. or from 550 to 600° C. or from 600 to 650° C. Preferably, the calcination conditions according to (viii) comprise a calcination atmosphere comprising oxygen, preferably air or lean air, more preferably air.

The respectively obtained zeolitic material having framework type BEA comprises, preferably essentially consists of, tin, boron, silicon, oxygen, and hydrogen. Therefore, in particular, the present invention also relates to a process for preparing a tin-containing zeolitic material having framework type BEA, the process comprising (i) providing an aqueous synthesis mixture comprising sources of tin, boron and silicon, and a framework type BEA structure directing agent; said step (i) preferably comprising
  (i.1) providing an aqueous synthesis mixture comprising a boron source, a silicon source, and a framework type BEA structure directing agent, wherein the aqueous synthesis mixture does not comprise a tin source;
  (i.2) subjecting the synthesis mixture provided in (i) to hydrothermal pre-crystallization conditions;
  (i.3) adding the tin source to the mixture obtained from (i.2);
(ii) subjecting the aqueous synthesis mixture obtained from (i.3) to hydrothermal crystallization conditions, obtaining a tin- and boron-containing zeolitic material having framework type BEA comprised in its mother liquor;
(iii) separating the tin- and boron-containing zeolitic material having framework type BEA from its mother liquor, said step (iii) preferably comprising
  (iii.1) preparing an aqueous suspension comprising the mother liquor and the tin- and boron-containing zeolitic material having framework type BEA and having a pH in the range of from 6 to 8.5, preferably in the range of from 7 to 8;
  (iii.2) separating at least a portion of the liquid phase from the aqueous suspension;
  (iii.3) washing the tin- and boron-containing zeolitic material having framework type BEA obtained from (iii.2) with a washing agent, preferably water;
(iv) subjecting the tin- and boron-containing zeolitic material having framework type BEA obtained from (iii.3) to drying conditions;
(v) subjecting the tin- and boron-containing zeolitic material having framework type BEA to calcination conditions;
(vi) subjecting the tin- and boron containing zeolitic material having framework type BEA obtained from (iv) or (v), preferably from (v), to deboronation, obtaining a deboronated tin-containing zeolitic material, said step (vi) preferably comprising
  (vi.1) treating the tin-containing zeolitic material having framework type BEA with an acid;
  (vi.2) washing the acid-treated tin-containing zeolitic material having framework type BEA with a washing agent, preferably water;
  or comprising
  (vi.1) treating the tin-containing zeolitic material having framework type BEA with water which does not contain an acid;
  (vi.2) optionally washing the water-treated tin-containing zeolitic material having framework type BEA with a washing agent, preferably water;
(vii) subjecting the tin-containing zeolitic material having framework type BEA obtained from (vi) to drying conditions;

(viii) subjecting the tin-containing zeolitic material having framework type BEA obtained from (vi) or (vii), preferably from (vii), to calcination conditions.

Accordingly, the present invention also relates to a tin-containing zeolitic material having framework type BEA which is obtainable or obtained by a process as described above.

Further, the present invention relates to a tin-containing zeolitic material having framework type BEA, having a tin content in the range of from 0.5 to 10 weight-%, calculated as elemental tin and based on the total weight of the tin-containing zeolitic material having framework type BEA, and having a boron content in the range of from 0 to 0.15 weight-%, calculated as elemental boron and based on the total weight of the tin- and boron-containing zeolitic material having framework type BEA, wherein at least 99 weight-%, preferably at least 99.5 weight-%, more preferably at least 99.9 weight-% of the zeolitic framework consist of Sn, optionally B, Si, O, and H, having a crystallinity of at least 50%, as determined according to XRD, preferably as defined in Reference Example 5 herein, having a water uptake in the range of from 15 to 35 weight-%, as determined via water adsorption-desorption isotherms, preferably as defined in Reference Example 4 herein, and having an absorption band with a maximum in the range of from 200 to 220 nm and optionally a further absorption band with a maximum in the range of from 230 to 300 nm, as determined according to UV-VIS, preferably as defined in Reference Example 2 herein.

Depending on the intended use of the tin- and boron-containing zeolitic material having framework type BEA or the tin-containing zeolitic material having framework type BEA according to the present invention, it may desirable to subject the respective zeolitic materials to shaping, thus obtaining a molding. For said shaping, it is conceivable to use binder or precursor of a binder, obtaining the moldings which comprise the zeolitic material having framework type BEA and the binder. Conceivable moldings include, but are not restricted to, extrudates, pellets, tablets, and the like.

Generally, the tin-containing zeolitic material having framework type BEA can be used for any suitable purpose. Preferably, it is used as a catalytically active material, preferably as a catalytically active material in oxidation reactions including Baeyer-Villiger-type oxidation reactions and Oppenauer-type oxidation reactions, reduction reactions including Meerwein-Ponndorf-Verley-type reduction reactions, aldol condensation reactions, retro-aldol reactions including the reaction of glucose to lactic acid, isomerization reactions including the isomerization of glucose to fructose, in particular for Baeyer-Villiger-type oxidation reactions.

For the above mentioned uses, also the respective moldings discussed above may be employed.

The present invention is further illustrated by the following set of embodiments and combinations of embodiments resulting from the given dependencies and back-references.

1. A process for preparing a tin-containing zeolitic material having framework type BEA, comprising
   (i) providing an aqueous synthesis mixture comprising sources of tin, boron and silicon, and a framework type BEA structure directing agent;
   (ii) subjecting the aqueous synthesis mixture provided in (i) to hydrothermal crystallization conditions, obtaining a tin-containing zeolitic material having framework type BEA comprised in its mother liquor.

2. A process for preparing a tin-containing zeolitic material having framework type BEA, preferably the process of embodiment 1, comprising
   (i.1) providing an aqueous synthesis mixture comprising a boron source, a silicon source, and a BEA structure directing agent;
   (i.2) subjecting the synthesis mixture provided in (i) to hydrothermal pre-crystallization conditions;
   (i.3) adding the tin source to the mixture obtained from (i.2);
   (ii) subjecting the aqueous synthesis mixture obtained from (i.3) to hydrothermal crystallization conditions, obtaining a tin-containing zeolitic material having framework type BEA comprised in its mother liquor.

3. The process of embodiment 2, wherein at least 99 weight-%, preferably at least 99.5 weight-%, more preferably at least 99.9 weight-% of the aqueous synthesis mixture provided in (i.1) consist of water, the boron source, the silicon source, and the framework type BEA structure directing agent.

4. The process of embodiment 2 or 3, wherein at least 99 weight-%, preferably at least 99.5 weight-%, more preferably at least 99.9 weight-% of the aqueous synthesis mixture subjected to hydrothermal crystallization conditions in (ii) consist of the mixture obtained from (i.3) and the tin source.

5. The process of any one of embodiments 2 to 4, wherein the hydrothermal pre-crystallization conditions according to (i.2) comprise a hydrothermal pre-crystallization temperature in the range of from 100 to 200° C., preferably in the range of from 110 to 190° C., more preferably in the range of from 120 to 180° C.

6. The process of any one of embodiments 2 to 5, wherein the hydrothermal pre-crystallization conditions according to (i.2) comprise an absolute hydrothermal pre-crystallization pressure in the range of from 1 to 30 bar.

7. The process of any one of embodiments 2 to 6, wherein the hydrothermal pre-crystallization conditions according to (i.2) comprise a hydrothermal pre-crystallization time in the range of from 6 to 72 h, preferably in the range of from 9 to 60 h, more preferably in the range of from 12 to 48 h.

8. The process of any one of embodiments 2 to 7, wherein the hydrothermal pre-crystallization conditions according to (i.2) do not comprise seeding.

9. The process of any one of embodiments 1 to 8, wherein the tin source is one or more of tin(II) alkoxides, tin(IV) alkoxides, tin(II) salts of organic acids, tin(IV) salts of organic acids, tin(II) salts of inorganic acids, tin(IV) salts of inorganic acids, preferably one or more of $SnCl_4$, Sn(IV)-acetate, Sn(IV)-tert-butoxide, $SnBr_4$, $SnF_4$, Sn(IV)-bisacetylacetonate dichloride; Sn(IV)-bisacetylacetonate dibromide, Sn(II)acetate, Sn(II)-acetylacetonate, Sn(II)-citrate, $SnCl_2$, $SnF_2$, $SnI_2$, $SnSO_4$, wherein the tin source preferably more comprises, more preferably is Sn(II)-acetate or Sn(IV)-tert-butoxide.

10. The process of any one of embodiments 1 to 9, wherein the boron source is one or more of boric acid, borates, boron halides, and boron oxide ($B_2O_3$), wherein the boron source preferably comprises, more preferably is, boric acid.

11. The process of any one of embodiments 1 to 10, wherein the silicon source is one or more of fumed silica and colloidal silica, wherein the silicon source preferably comprises, more preferably is, colloidal silica, and wherein the silicon source more preferably comprises, more preferably is, ammonia-stabilized colloidal silica.

12. The process of any one of embodiments 1 to 11, wherein the framework type BEA structure directing agent comprises, preferably is, tetraethylammonium hydroxide.
13. The process of any one of embodiments 1 to 12, wherein in the aqueous synthesis mixture provided in (i), preferably in (i.1), the weight ratio of boron relative to silicon is in the range of from 0.4:1 to 2.0:1, preferably in the range of from 0.6:1 to 1.7:1, more preferably in the range of from 0.9:1 to 1.4:1.
14. The process of any one of embodiments 1 to 13, wherein in the aqueous synthesis mixture provided in (i), preferably in (i.1), the weight ratio of the framework type BEA structure directing agent relative to silicon is in the range of from 0.10:1 to 0.30:1, preferably in the range of from 0.15:1 to 0.27:1, more preferably in the range of from 0.20:1 to 0.24:1.
15. The process of any one of embodiments 1 to 14, wherein in the aqueous synthesis mixture provided in (i), preferably in the mixture obtained from (i.3), the weight ratio of tin relative to silicon is in the range of from 0.005:1 to 0.1:1, preferably in the range of from 0.01:1 to 0.06:1, more preferably in the range of from 0.02:1 to 0.05:1.
16. The process of any one of embodiments 1 to 15, wherein the aqueous synthesis mixture subjected to hydrothermal crystallization conditions in (ii) comprises at most 0.1 weight-%, preferably at most 0.05 weight-% aluminum, calculated as elemental Al and based on the total weight of the aqueous synthesis mixture.
17. The process of any one of embodiments 1 to 16, wherein the aqueous synthesis mixture subjected to hydrothermal crystallization conditions in (ii) has a fluoride content of at most 0.1 weight-%, preferably at most 0.05 weight-%, calculated as elemental F and based on the total weight of the aqueous synthesis mixture.
18. The process of any one of embodiments 1 to 17, wherein the aqueous synthesis mixture subjected to hydrothermal crystallization conditions in (ii) has total content of alkali metal and alkaline earth metal of at most 0.1 weight-%, preferably at most 0.05 weight-% calculated as elemental alkali metal and alkaline earth metal and based on the total weight of the aqueous synthesis mixture.
19. The process of any one of embodiments 1 to 18, wherein the aqueous synthesis mixture subjected to hydrothermal crystallization conditions in (ii) has a hydrogen peroxide content of at most 0.01 weight-%, preferably at most 0.001 weight-%, more preferably of 0 weight-%, based on the total weight of the aqueous synthesis mixture.
20. The process of any one of embodiments 1 to 19, wherein the hydrothermal crystallization conditions according to (ii) comprise a hydrothermal crystallization temperature in the range of from 100 to 200° C., preferably in the range of from 110 to 190° C., more preferably in the range of from 120 to 180° C.
21. The process of any one of embodiments 1 to 20, wherein the hydrothermal crystallization conditions according to (ii) comprise an absolute hydrothermal crystallization pressure in the range of from 1 to 30 bar.
22. The process of any one of embodiments 1 to 21, wherein the hydrothermal crystallization conditions according to (ii) comprise a hydrothermal crystallization time in the range of from 6 to 240 h, preferably in the range of from 9 to 180 h, more preferably in the range of from 12 to 120 h.
23. The process of any one of embodiments 1 to 22, wherein the hydrothermal crystallization conditions according to (ii) do not comprise seeding.
24. The process of any one of embodiments 1 to 23, further comprising
    (iii) separating the tin-containing zeolitic material having framework type BEA from its mother liquor.
25. The process of embodiment 24, wherein the separating according to (iii) comprises washing the tin-containing zeolitic material having framework type BEA with a washing agent, preferably water.
26. The process of embodiment 23, wherein the separating according to (iii) comprises
    (iii.1) preparing an aqueous suspension comprising the mother liquor and the tin-containing zeolitic material having framework type BEA and having a pH in the range of from 6 to 8.5, preferably in the range of from 7 to 8;
    (iii.2) separating at least a portion of the liquid phase from the aqueous suspension;
    (iii.3) washing the tin-containing zeolitic material having framework type BEA obtained from (iii.2) with a washing agent, preferably water.
27. The process of any one of embodiments 1 to 26, preferably of any one of embodiments 24 to 26, further comprising
    (iv) subjecting the tin-containing zeolitic material having framework type BEA to drying conditions.
28. The process of embodiment 27, wherein the drying conditions according to (iv) comprise a drying temperature in the range of from 60 to 200° C., preferably in the range of from 80 to 190° C., more preferably in the range of from 100 to 180° C.
29. The process of embodiment 27 or 28, wherein the drying conditions according to (iv) comprise a drying atmosphere comprising oxygen, preferably air or lean air, more preferably air.
30. The process of embodiment 27 or 28, wherein the drying conditions according to (iv) comprise a drying atmosphere comprising nitrogen, wherein more preferably, the atmosphere is technical nitrogen.
31. The process of any one of embodiments 1 to 30, preferably of any one of embodiments 23 to 30, more preferably of any one of embodiments 27 to 30, further comprising
    (v) subjecting the tin-containing zeolitic material having framework type BEA to calcination conditions.
32. The process of embodiment 31, wherein the calcination conditions according to (v) comprise a calcination temperature in the range of from 400 to 700° C., preferably in the range of from 420 to 680° C., more preferably in the range of from 450 to 650° C.
33. The process of embodiment 31 or 32, wherein the calcination conditions according to (v) comprise a calcination atmosphere comprising oxygen, preferably air or lean air, more preferably air.
34. The process of any one of embodiments 1 to 33, being a process for preparing a tin- and boron-containing zeolitic material having framework type BEA.
35. The process of any one of embodiments 1 to 33, preferably of any one of embodiments 24 to 33, more preferably of any one of embodiments 27 to 33, more preferably of any one of embodiments 31 to 33, further comprising
    (vi) subjecting the tin-containing zeolitic material having framework type BEA to deboronation, obtaining a deboronated tin-containing zeolitic material.
36. The process of embodiment 35, wherein the deboronation according to (vi) comprises (vi.1) treating the tin-containing zeolitic material having framework type BEA with an acid;
(vi.2) washing the acid-treated tin-containing zeolitic material having framework type BEA with a washing agent, preferably water.

37. The process of embodiment 35, wherein the deboronation according to (vi) comprises
(vi.1) treating the tin-containing zeolitic material having framework type BEA with water which does not contain an acid;
(vi.2) optionally washing the water-treated tin-containing zeolitic material having framework type BEA with a washing agent, preferably water.

38. The process of embodiment 36 or 37, wherein the acid according to (vi.1) is an inorganic acid or an organic acid, preferably including one or more of sulfuric acid, hydrochloric acid, and nitric acid, more preferably comprising, more preferably being, nitric acid.

39. The process of any one of embodiments 36 to 38, wherein the treating according to (vi.1) is carried out in an aqueous mixture comprising the tin-containing zeolitic material having framework type BEA.

40. The process of any one of embodiments 36 to 39, wherein the treating according to (vi.1) is carried out at a temperature, preferably a temperature of the aqueous mixture comprising the tin-containing zeolitic material having framework type BEA, in the range of from 60 to 100° C., preferably in the range of from 80 to 100° C., more preferably in the range of from 90 to 100° C.

41. The process of embodiment 40, wherein the treating according to (vi.1) is carried out under reflux.

42. The process of any one of embodiments 36 to 41, further comprising
(vii) subjecting the deboronated tin-containing zeolitic material having framework type BEA to drying conditions.

43. The process of embodiment 42, wherein the drying conditions according to (vii) comprise a drying temperature in the range of from 60 to 200° C., preferably in the range of from 80 to 190° C., more preferably in the range of from 100 to 180° C.

44. The process of embodiment 42 or 43, wherein the drying conditions according to (vii) comprise a drying atmosphere comprising nitrogen, preferably nitrogen, air, or lean air.

45. The process of embodiment 42 or 43, wherein the drying conditions according to (vii) comprise a drying atmosphere comprising nitrogen, wherein more preferably, the atmosphere is technical nitrogen.

46. The process of any one of embodiments 35 to 45, preferably of any one of embodiments 42 to 45, further comprising
(viii) subjecting the deboronated tin-containing zeolitic material having framework type BEA to calcination conditions.

47. The process of embodiment 46, wherein the calcination conditions according to (viii) comprise a calcination temperature in the range of from 400 to 700° C., preferably in the range of from 420 to 680° C., more preferably in the range of from 450 to 650° C.

48. The process of embodiment 46 or 47, wherein the calcination conditions according to (viii) comprise a calcination atmosphere comprising oxygen, preferably air or lean air, more preferably air.

49. The process of any one of embodiments 1 to 48, preferably of any one of embodiments 42 to 48, more preferably of any one of embodiments 46 to 48, further comprising
(ix) shaping the tin-containing zeolitic material having framework type BEA, obtaining moldings.

50. The process of embodiment 49, wherein the shaping according to (vi) is carried out using a binder or precursor of a binder, obtaining the moldings which comprise the tin-containing zeolitic material having framework type BEA and the binder.

51. A tin-containing zeolitic material having framework type BEA, preferably a tin- and boron-containing zeolitic material having framework type BEA, obtainable or obtained according to a process of any one of embodiments 1 to 34.

52. A tin-containing zeolitic material having framework type BEA, obtainable or obtained according to a process of any one of embodiments 35 to 48.

53. A molding comprising a tin-containing zeolitic material having framework type BEA, obtainable or obtained according to a process of embodiment 49 or 50.

54. A tin- and boron-containing zeolitic material having framework type BEA, having a tin content in the range of from 0.5 to 10 weight-%, calculated as elemental tin and based on the total weight of the tin- and boron-containing zeolitic material having framework type BEA, and having a boron content in the range of from 0.5 to 9 weight-%, calculated as elemental boron and based on the total weight of the tin- and boron-containing zeolitic material having framework type BEA.

55. The tin- and boron-containing zeolitic material having framework type BEA of embodiment 54, having a tin content in the range of from 0.75 to 9 weight-%, preferably in the range of from 1 to 8 weight-%, more preferably in the range of from 1.5 to 7.5 weight-%.

56. The tin- and boron-containing zeolitic material having framework type BEA of embodiment 54 or 55, having a boron content in the range of from 0.75 to 8 weight-%, preferably in the range of from 1 to 7 weight-%.

57. The tin- and boron-containing zeolitic material having framework type BEA of any one of embodiments 54 to 56, wherein at least 99 weight-%, preferably at least 99.5 weight-%, more preferably at least 99.9 weight-% of the zeolitic framework consist of Sn, B, Si, O, and H.

58. The tin- and boron-containing zeolitic material having framework type BEA of any one of embodiments 54 to 56, being calcined.

59. The tin- and boron-containing zeolitic material having framework type BEA of any one of embodiments 54 to 58, having a BET specific surface of at least 400 m$^2$/g, preferably in the range of from 400 to 600 m$^2$/g, preferably in the range of from 450 to 550 m$^2$/g, as determined according to DIN 66131.

60. The tin- and boron-containing zeolitic material having framework type BEA of any one of embodiments 54 to 59, having a crystallinity of at least 50%, preferably of at least 55%, more preferably in the range of from 55 to 85%, more preferably in the range of from 60 to 85%, more preferably in the range of from 65 to 85%, as determined according to XRD, preferably as defined in Reference Example 5 herein.

61. The tin- and boron-containing zeolitic material having framework type BEA of any one of embodiments 54 to 60, having a micropore volume in the range of from 0.10 to 0.25 cm$^3$/g, as determined according to DIN 66135.

62. The tin- and boron-containing zeolitic material having framework type BEA of any one of embodiments 54 to 61, having a mean crystal size of at most 100 nm, preferably in the range of from 5 to 100 nm, as determined according to SEM, preferably as defined in Reference Example 1 herein.
63. The tin- and boron-containing zeolitic material having framework type BEA of any one of embodiments 54 to 62, having an absorption band with a maximum in the range of from 200 to 220 nm and optionally a further absorption band with a maximum in the range of from 230 to 300 nm, as determined according to UV-VIS, preferably as defined in Reference Example 2 herein.
64. The tin- and boron-containing zeolitic material having framework type BEA of any one of embodiments 54 to 63, wherein in the FT-IR spectrum preferably determined as defined in Reference Example 3 herein, the ratio of the absorption maximum of a first band with a maximum in the range of from 3700 to 3750 $cm^{-1}$ relative to the absorption maximum of a second band with a maximum in the range of from 3550 to 3699 $cm^{-1}$ is in the range of from 0.5 to 2.0, preferably in the range of from 0.7 to 1.5.
65. The tin- and boron-containing zeolitic material having framework type BEA of any one of embodiments 54 to 64, having a water uptake of at least 10 weight-%, preferably in the range from 10 to 35 weight-%, more preferably in the range from 15 to 35 weight-%, more preferably in the range from 20 to 35 weight-%, as determined via water adsorption-desorption isotherms, preferably as defined in Reference Example 4 herein.
66. The tin- and boron-containing zeolitic material having framework type BEA of any one of embodiments 54 to 65, characterized by an XRD spectrum comprising peaks at 2 theta diffraction angles of (8.0±0.1°), (22.0±0.1°), (23.0±0.1°), (25.9±0.1°), (27.3±0.1°).
67. A tin-containing zeolitic material having framework type BEA having a tin content in the range of from 0.5 to 10 weight-%, calculated as elemental tin and based on the total weight of the tin-containing zeolitic material having framework type BEA, and having a boron content in the range of from 0 to 0.15 weight-%, calculated as elemental boron and based on the total weight of the tin- and boron-containing zeolitic material having framework type BEA, wherein at least 99 weight-%, preferably at least 99.5 weight-%, more preferably at least 99.9 weight-% of the zeolitic framework consist of Sn, B, Si, O, and H,
having a crystallinity of at least 50%, as determined according to XRD, preferably as defined in Reference Example 5 herein,
having a water uptake in the range of from 15 to 35 weight-%, as determined via water adsorption-desorption isotherms, preferably as defined in Reference Example 4 herein,
and having an absorption band with a maximum in the range of from 200 to 220 nm and optionally a further absorption band with a maximum in the range of from 230 to 300 nm, as determined according to UV-VIS, preferably as defined in Reference Example 2 herein.
68. A molding comprising a tin-containing zeolitic material having framework type BEA according to any one of embodiments 54 to 66 or according to embodiment 67 and optionally a binder.
69. Use of a tin- and boron-containing zeolitic material having framework type BEA according to embodiment 51 or according to any one of embodiments 54 to 66 as a catalytically active material, preferably as a bifunctional catalytically active material, more preferably as a bifunctional catalytically active material in a reaction for which a catalytically active acid function is combined with a catalytically active redox function of the catalytically active material.
70. Use of a tin-containing zeolitic material having framework type BEA according to embodiment 52 or 67 as a catalytically active material, preferably as a catalytically active material in oxidation reactions including Baeyer-Villiger-type oxidation reactions and Oppenauer-type oxidation reactions, reduction reactions including Meerwein-Ponndorf-Verley-type reduction reactions, aldol condensation reactions, retro-aldol reactions including the reaction of glucose to lactic acid, isomerization reactions including the isomerization of glucose to fructose.
71. Use of a molding according to embodiment 53 or 68 as a catalyst, preferably as a catalyst in oxidation reactions including Baeyer-Villiger-type oxidation reactions and Oppenauer-type oxidation reactions, reduction reactions including Meer-wein-Ponndorf-Verley-type reduction reactions, aldol condensation reactions, retro-aldol reactions including the reaction of glucose to lactic acid, isomerization reactions including the isomerization of glucose to fructose.
72. The use of embodiment 70 or 71 for Baeyer-Villiger-type oxidation reactions.
73. A catalytic oxidation reaction, including a Baeyer-Villiger-type oxidation reaction and an Oppenauer-type oxidation reaction, a reduction reaction including a Meerwein-Ponndorf-Verley-type reduction reaction, an aldol condensation reaction, a retro-aldol reaction including the reaction of glucose to lactic acid, an isomerization reactions including the isomerization of glucose to fructose, wherein as catalytically active material, a tin-containing zeolitic material having framework type BEA according to embodiment 52 or 67 is employed.
74. A catalytic oxidation reaction, including a Baeyer-Villiger-type oxidation reaction and an Oppenauer-type oxidation reaction, a reduction reaction including a Meerwein-Ponndorf-Verley-type reduction reaction, an aldol condensation reaction, a retro-aldol reaction including the reaction of glucose to lactic acid, an isomerization reactions including the isomerization of glucose to fructose, wherein as catalyst, a molding according to embodiment 53 or 68 is employed.
75. The catalytic oxidation reaction of embodiment 73 or 74, being a Baeyer-Villiger-type oxidation reaction.

The present invention is further illustrated by the following reference examples and examples.

EXAMPLES

Reference Example 1: SEM Measurements

The SEM measurements were performed as follows: Powder samples were investigated with the field emission scanning electron microscope (FESEM) Jeol JSM 7500 TFE, which run at acceleration voltages from 5 kV. The powder samples were prepared on a standard SEM stub and sputter coated with 9 nm platinum layer. The sputter coater was the Baltec SCD 500.

Reference Example 2: UV-VIS Measurements

The UV-VIS measurements were performed using a PerkinElmer Lambda 950 equipped with a Labsphere 150 mm integrating sphere for the measurement of diffuse reflection (gloss trap closed). The powder cuvette used for the solid samples was filled with the solid samples so that the area measured was completely covered by the sample. As reference, Spectralon standard was used, integration time 0.2 s, scan speed 267 nm/min, spectral range 200-800 nm, measurement at room temperature. The spectra obtained were transformed to Kubelka-Munk spectra.

Reference Example 3: FT-IR Measurements

The FT-IR (Fourier-Transformed-Infrared) measurements were performed on a Nicolet 6700 spectrometer. The powdered material was pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 4: Determination of the Water Uptake

Water adsorption/desorption isotherms were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept isothermal during the measurement. The microbalance was calibrated, and the weight of the dried sample was balanced (maximum mass deviation 0.01 weight-%). Water uptake by the sample was measured as the increase in weight over that of the dry sample. First, as adsorption curve was measured by increasing the relative humidity (RH) (expressed as weight-% water in the atmosphere inside of the cell) to which the sample was exposed and measuring the water uptake by the sample as equilibrium. The RH was increased with a step of 10 weight-% from 5% to 85% and at each step the system controlled the RH and monitored the sample weight until reaching the equilibrium conditions after the sample was exposed from 85 weight-% to 5 weight-% with a step of 10% and the change in the weight of the sample (water uptake) was monitored and recorded.

Reference Example 5: Determination of the Crystallinity

The crystallinity was determined according to the method as described in the User Manual DIFFRAC.EVA Version 3, page 105, from Bruker AXS GmbH, Karlsruhe (published February 2003). The respective data were collected on a standard Bruker D8 Advance Diffractometer Series II using a LYNXEYE detector, from 2° to 50° 2theta, using fixed slits, a step size of 0.02° 2theta and a scan speed of 2.4 s/step. The parameters used for estimating the background/amorphous content were Curvature=0 and Threshold=0.8.

Example 1: Preparation of a Tin- and Boron-Containing Zeolitic Material Having a BEA Framework Structure by Direct Synthesis In a beaker, 90 g de-ionized water were admixed with 152.71 g tetraethylammonium hydroxide (35 weight-%, in water) under stirring at about 200 r.p.m. (revolutions per minute). After 10 min of stirring, 26.25 g boric acid (99.9%)) were added, and the resulting mixture was stirred until a clear solution was obtained (about 30 min). Then, 238.85 g Ludox® AS-40 were added (colloidal silica, 40 weight-% in water), and the resulting mixture was stirred overnight. The pH of the mixture was 10.7, as measured with a pH-sensitive glass electrode. The mixture was transferred to an autoclave and subjected to hydrothermal pre-crystallization at 160° C. for 48 h under stirring at 140 r.p.m. After cooling, 25 g Sn(IV)tert-butoxide were added (as solution in water), and the mixture was subjected to hydrothermal crystallization at 160° C. for 96 h under stirring at 140 r.p.m.

The resulting suspension comprising the tin- and boron-containing zeolitic material having a BEA framework structure in its mother liquor was removed from the autoclave and admixed with the double amount of water, resulting in a mixture having a pH of 8.9. Using nitric acid (10 weight-% in water), the pH of the mixture was adjusted to a value of 7-8. After filtration, the tin- and boron-containing zeolitic material having a BEA framework structure was washed with de-ionized water until the washing water had a conductivity of less than 150 microSiemens/cm.

The washed tin- and boron-containing zeolitic material having a BEA framework structure was then dried at 120° C. for 12 h and calcined at 490° C. for 5 h under air (heating ramp 2 K/min). 34.4 g of calcined tin- and boron-containing zeolitic material having a BEA framework structure were obtained.

Figure 2:
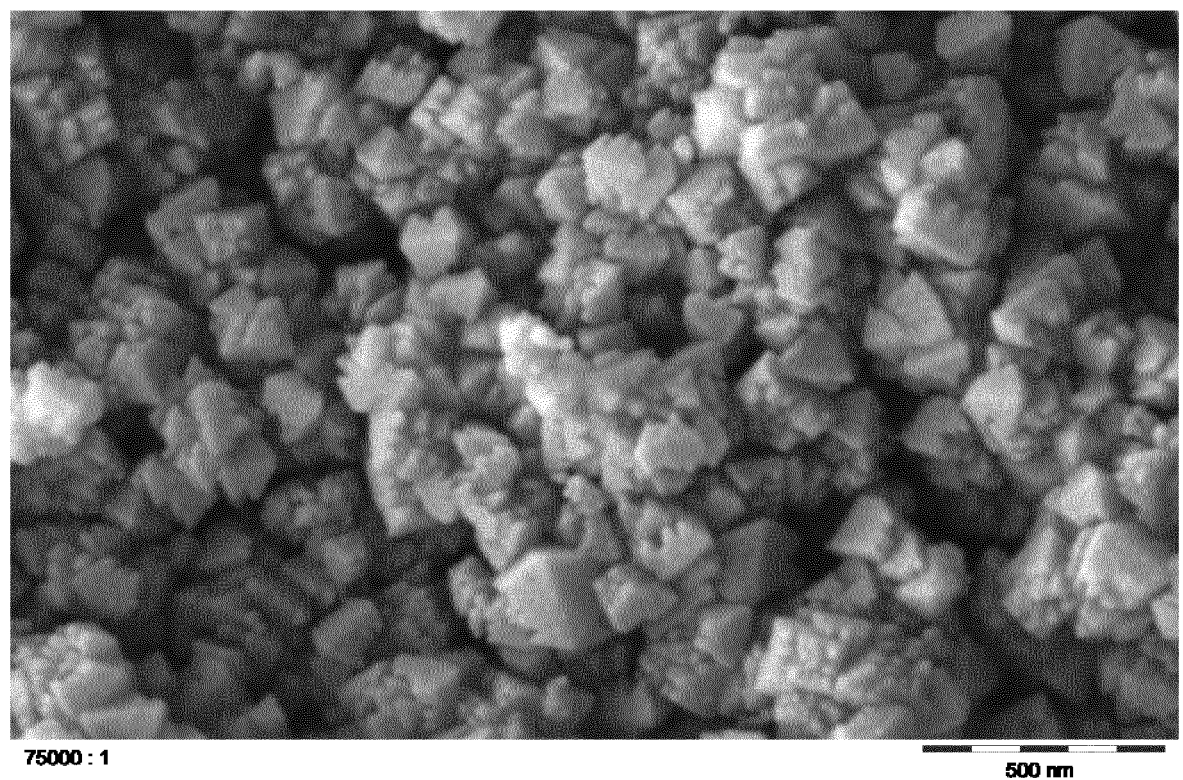
Figure 3:
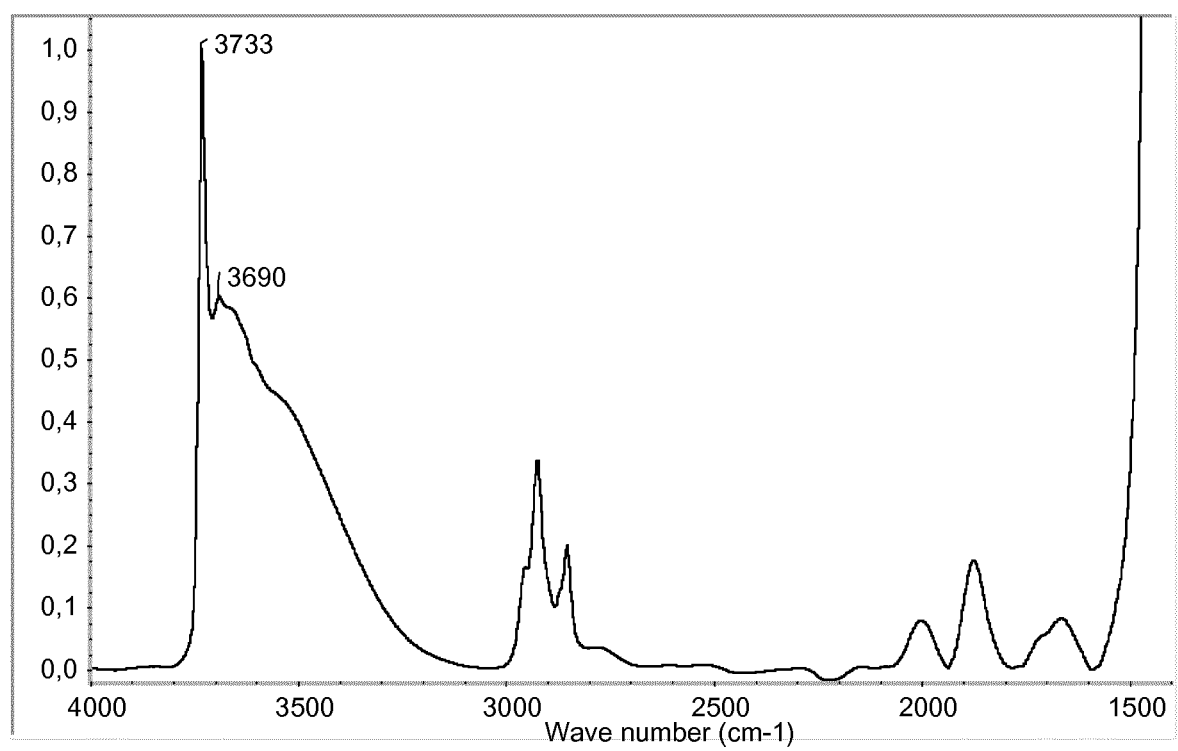
Figure 10:
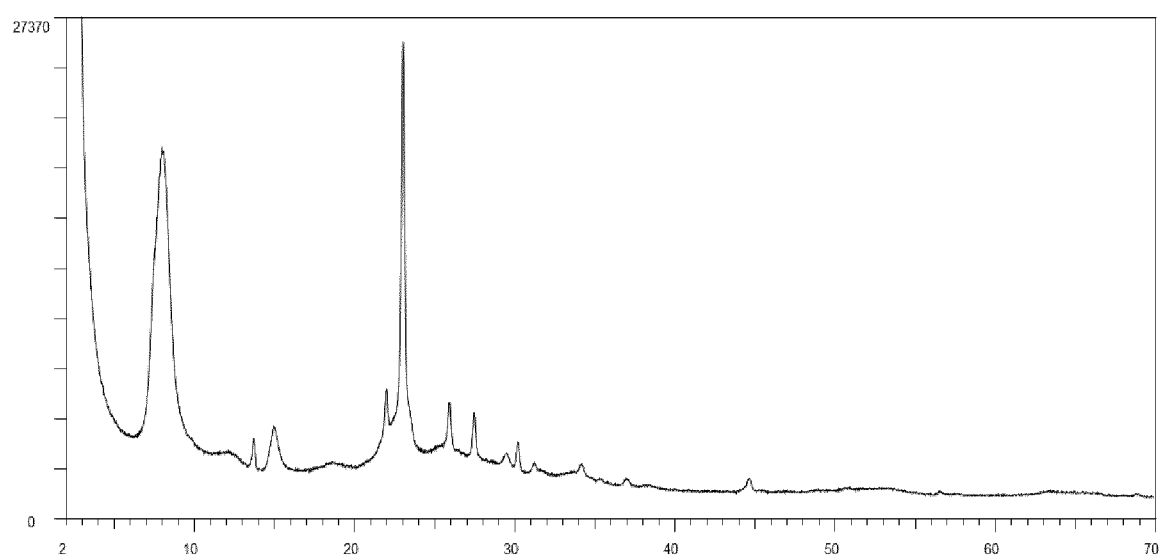

The tin- and boron-containing zeolitic material having a BEA framework structure had the following composition: 2.7 weight-% Sn, 1.3 weight-% B, 41 weight-% Si, <0.1 weight-% C (TOC). The BET surface as determined according to DIN 66131 was 487 $m^2$/g. The crystallinity, as determined according to Reference Example 5, was 68%. The water adsorption, as determined according to Reference Example 4, was 23.0 weight-%. The UV-VIS spectrum, as determined according to Reference Example 2, is shown in FIG. 1. An SEM picture, as determined according to Reference Example 1, is shown in FIG. 2. The FT-IR spectrum, as determined according to Reference Example 3, is shown in FIG. 3. The FT-IR ratio, defined as the ratio of the absorption maximum of a first band with a maximum in the range of from 3700 to 3750 $cm^{-1}$ relative to the absorption maximum of a second band with a maximum in the range of from 3550 to 3699 $cm^{-1}$, is 1.66. The XRD spectrum is shown in FIG. 10.

Example 2: Preparation of a Tin- and Boron-Containing Zeolitic Material Having a BEA Framework Structure by Direct Synthesis In a beaker, 129.5 g de-ionized water were admixed with 220.0 g tetraethylammonium hydroxide (35 weight-%, in water) under stirring at about 200 r.p.m. (revolutions per minute). After 10 min of stirring, 37.8 g boric acid (99.9%)) were added, and the resulting mixture was stirred until a clear solution was obtained (about 30 min). Then, 343.95 g Ludox® AS-40 were added (colloidal silica, 40 weight-% in water), and the resulting mixture was stirred overnight. The pH of the mixture was 10.7, as measured with a pH-sensitive glass electrode. The mixture was transferred to an autoclave and subjected to hydrothermal pre-crystallization at 160° C. for 48 h under stirring at 140 r.p.m. After cooling, 20.72 g Sn(II)acetate were added (as solution in water), and the mixture was subjected to hydrothermal crystallization at 160° C. for 96 h under stirring at 140 r.p.m.

The resulting suspension comprising the tin- and boron-containing zeolitic material having a BEA framework structure in its mother liquor was removed from the autoclave and admixed with the double amount of water, resulting in a mixture having a pH of 8.5. Using nitric acid (10 weight-% in water), the pH of the mixture was adjusted to a value of 7-8. After filtration, the tin- and boron-containing zeolitic material having a BEA framework structure was washed with de-ionized water until the washing water had a conductivity of less than 150 microSiemens/cm.

The washed tin- and boron-containing zeolitic material having a BEA framework structure was then dried at 120° C. for 12 h and calcined at 490° C. for 5 h under air (heating ramp 2 K/min). 146 g of calcined tin- and boron-containing zeolitic material having a BEA framework structure were obtained.

Figure 4:
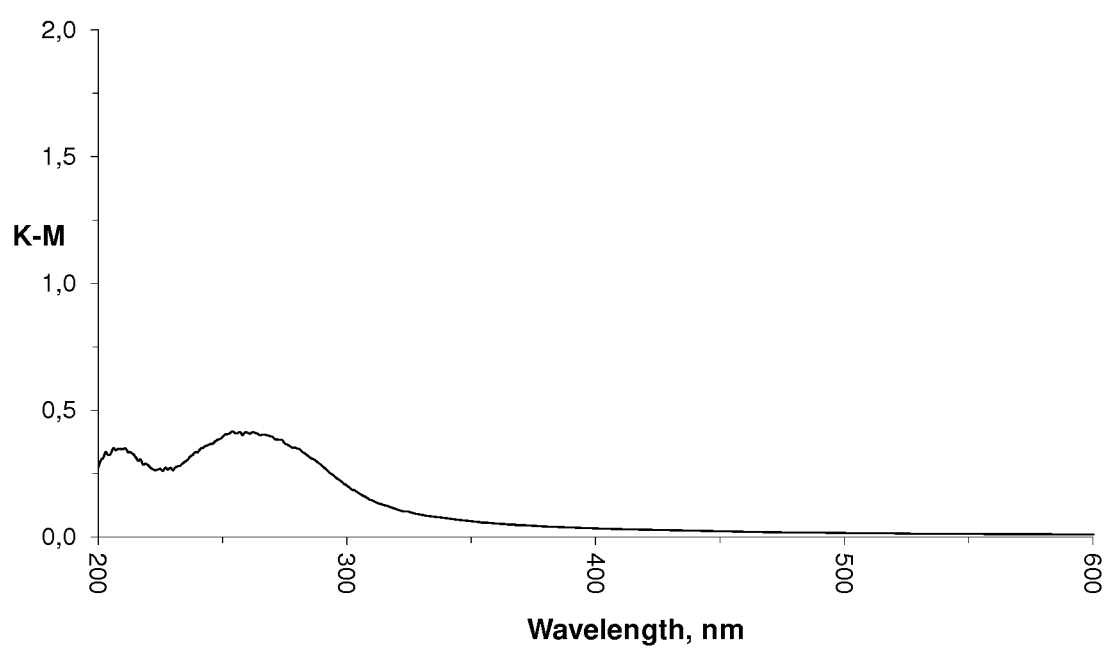

The tin- and boron-containing zeolitic material having a BEA framework structure had the following composition: 7.1 weight-% Sn, 1.3 weight-% B, 41 weight-% Si, <0.1 weight-% C (TOC). The BET surface as determined according to DIN 66131 was 457 m$^2$/g. The crystallinity, as determined according to Reference Example 5, was 69%. The water adsorption, as determined according to Reference Example 4, was 23.8 weight-%. The UV-VIS spectrum, as determined according to Reference Example 2, is shown in FIG. 4.

Figure 5:
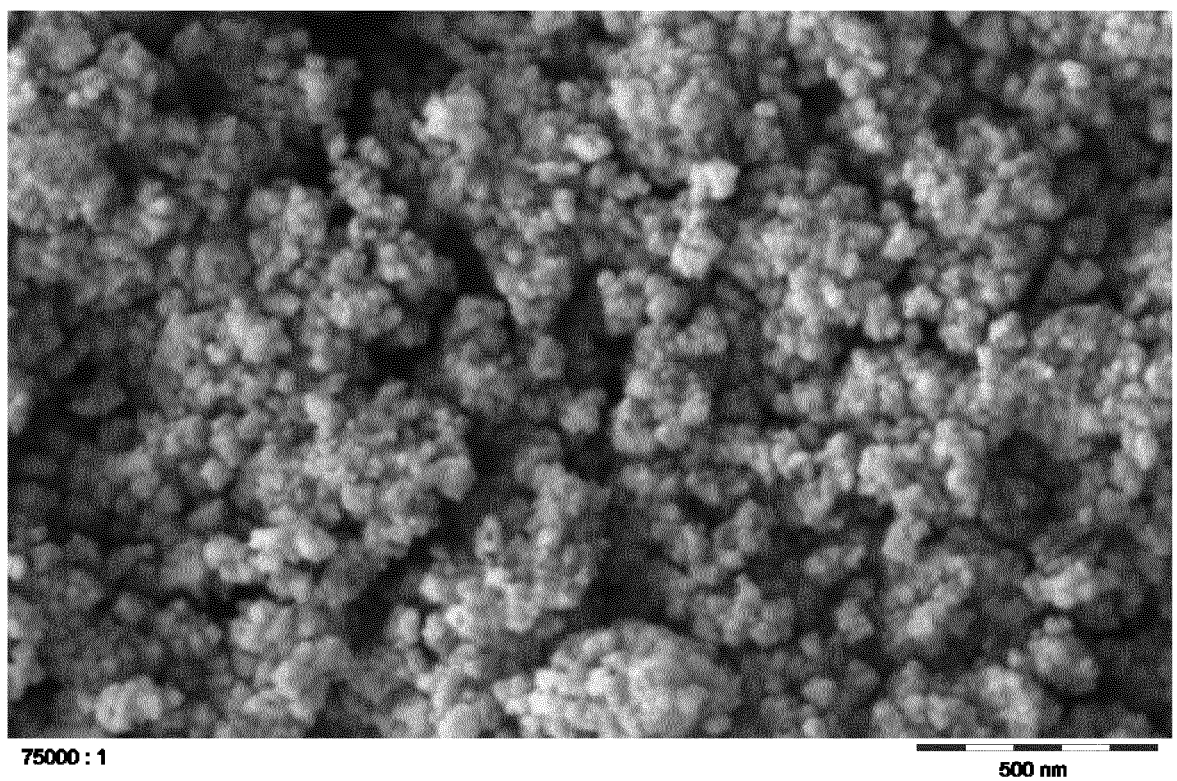
Figure 6:
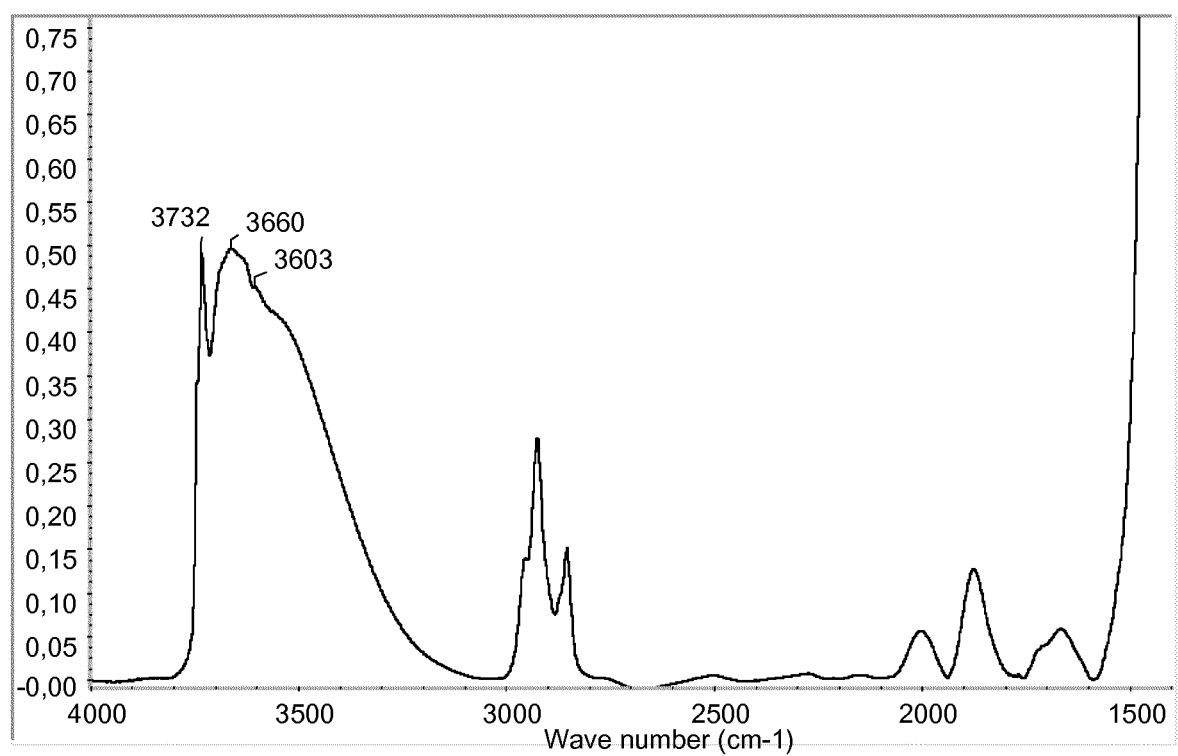

An SEM picture, as determined according to Reference Example 1, is shown in FIG. 5. The FT-IR spectrum, as determined according to Reference Example 3, is shown in FIG. 6. The FT-IR ratio, defined as the ratio of the absorption maximum of a first band with a maximum in the range of from 3700 to 3750 cm$^{-1}$ relative to the absorption maximum of a second band with a maximum in the range of from 3550 to 3699 cm$^{-1}$, is 0.98.

Example 3: Preparation of a Tin-Zeolitic Material Having a BEA Framework Structure by Deboronation of Tin- and Boron-Containing Zeolitic Material Having a BEA Framework Structure 676.92 g de-ionized water were passed in a 2 l stirred vessel. Under stirring, 40 g of the zeolitic material obtained from Example 2 above were added, and the resulting mixture heated to 100° C. The mixture was kept at this temperature under reflux for 1 h. Then, the mixture was cooled to room temperature. The cooled mixture was subjected to filtration and the filter cake was washed with de-ionized water until the washing water had a conductivity of less than 100 microSiemens/cm.

The thus obtained filter cake was subjected to drying at 120° C. for 10 h under air (heating ramp: 3 K/min), followed by calcination at 550° C. for 10 h under air at an air flow of 80 Nl/h (heating ramp: 2 K/min) (Nl/h is defined as flow rate of a gas measured at 101.325 kPa and 0° C. according to DIN 1343). 37.7 calcined g of deboronated tin-containing zeolitic material having a BEA framework structure were obtained.

Figure 7:
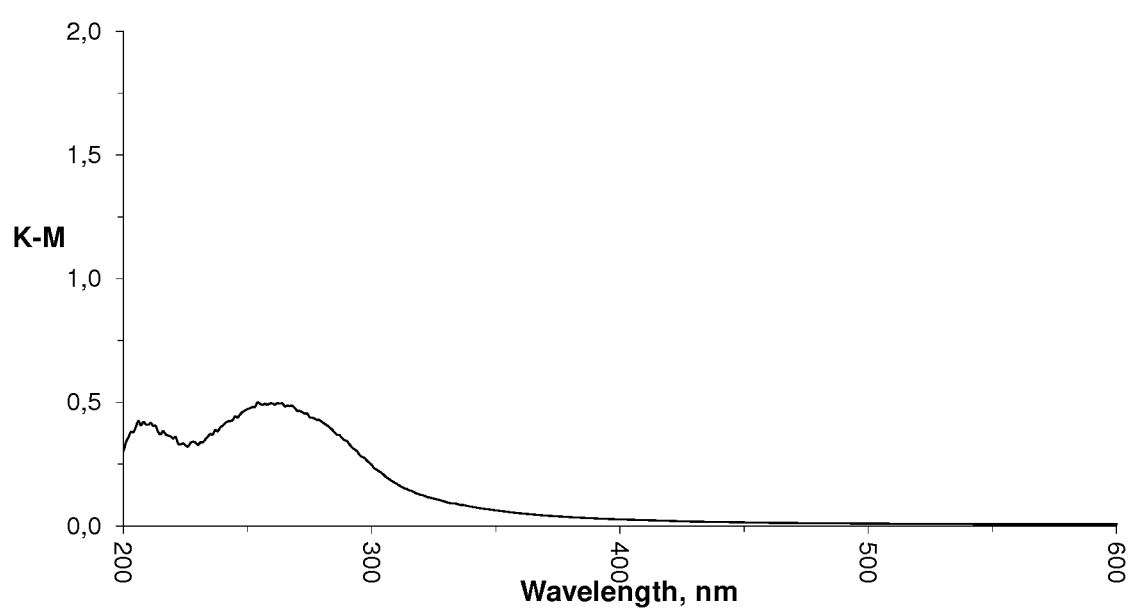
Figure 8:
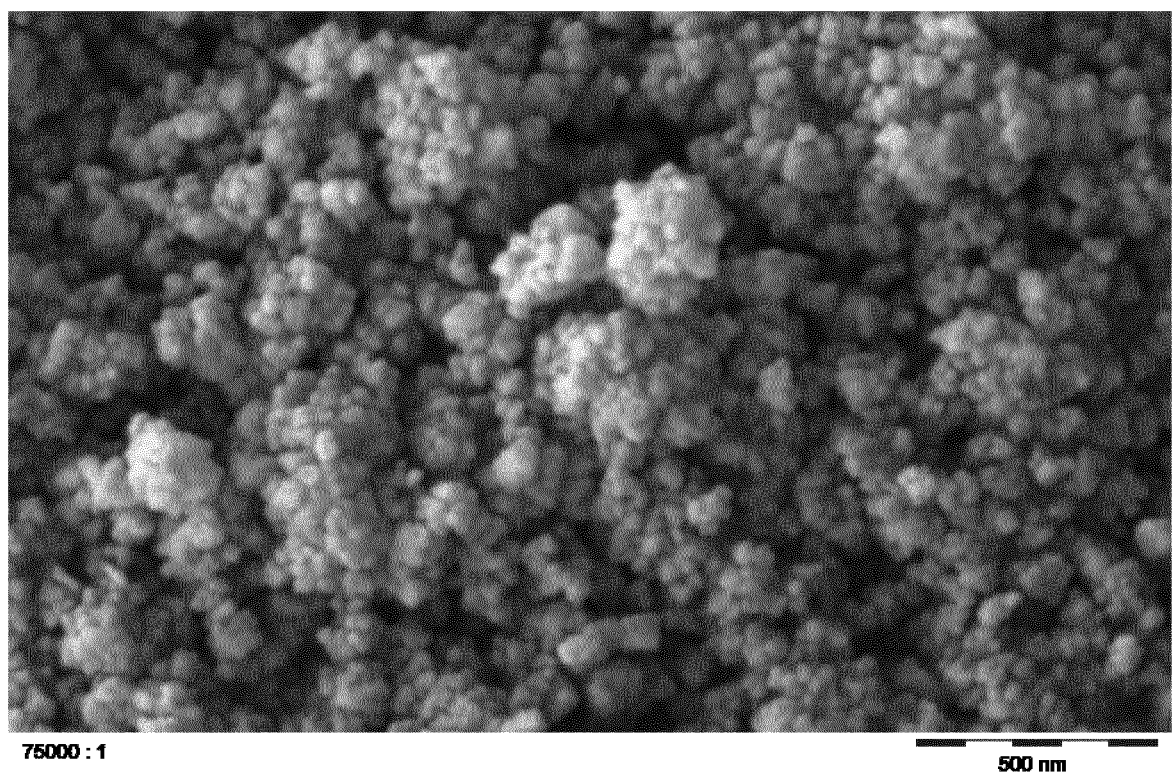
Figure 9:
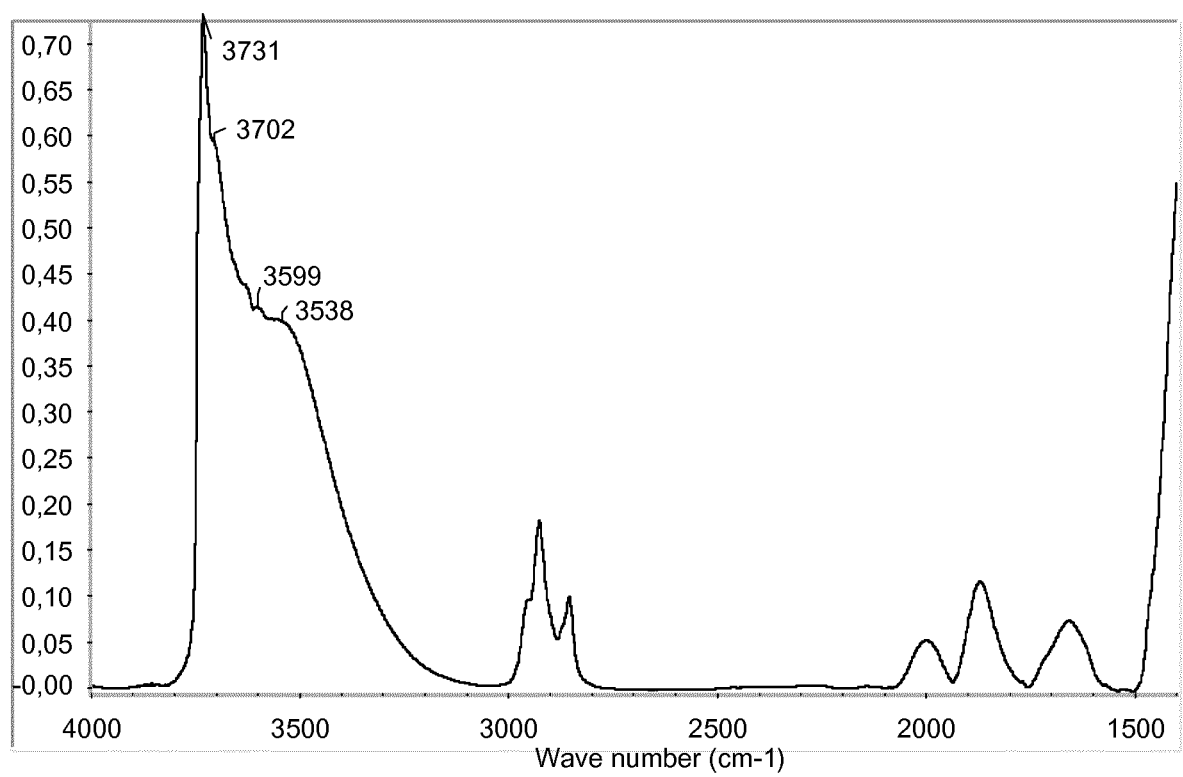
Figure 11:
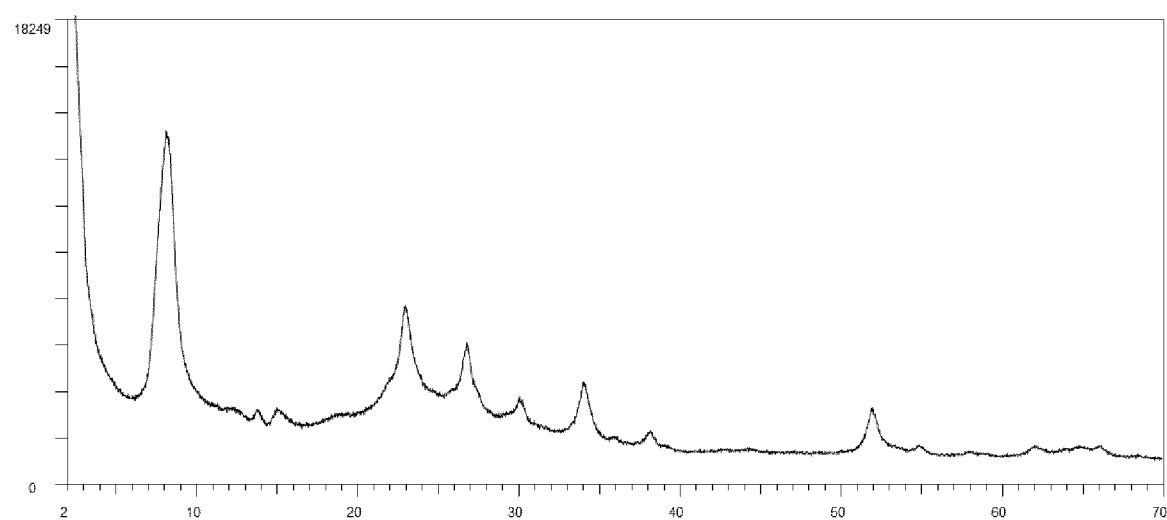

The deboronated tin-containing zeolitic material having a BEA framework structure had the following composition: 6.5 weight-% Sn, 0.13 weight-% B, 41 weight-% Si, <0.1 weight-% C (TOC). The BET surface as determined according to DIN 66131 was 458 m$^2$/g. The crystallinity, as determined according to Reference Example 5, was 56%. The water adsorption, as determined according to Reference Example 4, was 18 weight-%. The UV-VIS spectrum, as determined according to Reference Example 2, is shown in FIG. 7. An SEM picture, as determined according to Reference Example 1, is shown in FIG. 8. The FT-IR spectrum, as determined according to Reference Example 3, is shown in FIG. 9. The FT-IR ratio, defined as the ratio of the absorption maximum of a first band with a maximum in the range of from 3700 to 3750 cm$^{-1}$ relative to the absorption maximum of a second band with a maximum in the range of from 3550 to 3699 cm$^{-1}$, is 1.2. The XRD spectrum is shown in FIG. 11.

Example 4: Baeyer-Villiger Oxidation of Cylohexanone to Caprolactone Using a Tin-Containing Zeolitic Material Having a BEA Framework Structure A 100 mL glass flask was charged with cyclohexanone (1.5 g), the zeolitic material (0.1 g) and 1,4-dioxane as solvent (45 g) and heated to 95° C. An aqueous solution of hydrogen peroxide (70 w/w %, 0.49 g) was then added and the reaction mixture was stirred. After cooling to room temperature, the resulting solution was filtered and the filtrate was analyzed by GC using di-n-butylether as internal standard. The results are shown in Table 1 below.

TABLE 1

Results of Example 4

| Zeolitic material according to Example # | Reaction time/min | Sn content of zeolitic material/ weight-% | Cyclo-hexanone conver-sion/% | Selectivity [1] based on cyclo-hexanone/% |
|---|---|---|---|---|
| 1 | 240 | 2.7 | 14 | 14 |
| 3 | 240 | 6.5 | 10 | 57 |

[1] molar amount of caprolactone obtained from the reaction divided by the molar amount of cyclohexanone converted in the reaction Comparative Example 1: Preparation of a Tin- and Boron-Containing Material by Direct Synthesis without Pre-Crystallizing Under Hydrothermal Conditions In a beaker, 90 g de-ionized water were admixed with 152.71 g tetraethylammonium hydroxide (35 weight-%, in water) under stirring at about 200 r.p.m. (revolutions per minute). After 10 min of stirring, 26.25 g boric acid (99.9%) were added, and the resulting mixture was stirred until a clear solution was obtained (about 30 min). Then, 238.85 g Ludox® AS-40 were added (colloidal silica, 40 weight-% in water), and the resulting mixture was stirred overnight. The pH of the mixture was 10.7, as measured with a pH-sensitive glass electrode. The mixture was then stirred at 50° C. for 48 h at 140 r.p.m. After cooling, 25 g Sn(IV)tert-butoxide were added (as solution in water), and the mixture was subjected to hydrothermal crystallization at 160° C. for 96 h under stirring at 140 r.p.m.

The resulting suspension comprising the tin- and boron-containing material in its mother liquor was removed from the autoclave and admixed with the double amount of water, resulting in a mixture having a pH of 8.9. Using nitric acid (10 weight-% in water), the pH of the mixture was adjusted to a value of 7-8. After filtration, the tin- and boron-containing material was washed with de-ionized water until the washing water had a conductivity of less than 150 microSiemens/cm.

The washed tin- and boron-containing material was then dried at 120° C. for 12 h and calcined at 490° C. for 5 h under air (heating ramp 2 K/min). 63 g of calcined tin- and boron-containing material were obtained.

Figure 12:
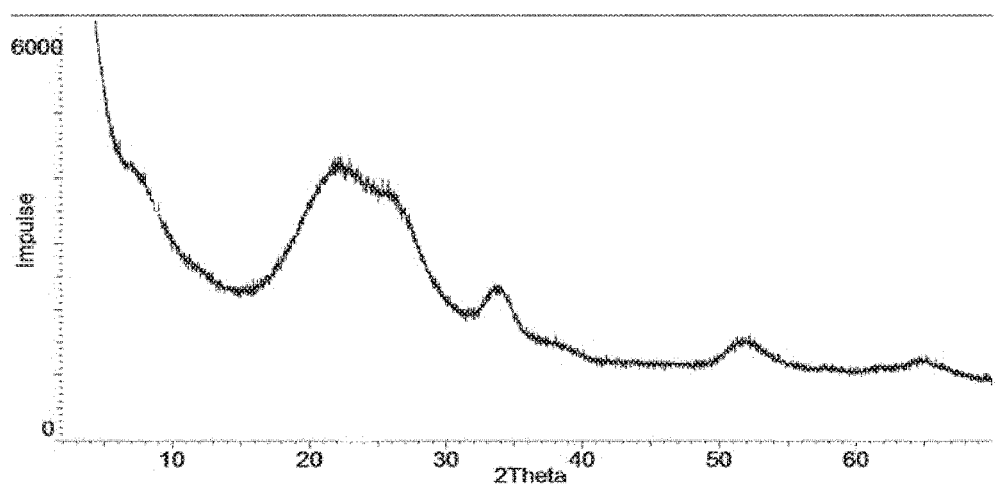

The tin- and boron-containing material had the following composition: 5.4 weight-% Sn, 0.61 weight-% B, 41 weight-% Si, <0.1 weight-% C (TOC). The BET surface as determined according to DIN 66131 was 234 $m^2/g$. The tin- and boron-containing material, as determined according to Reference Example 5, was amorphous. The XRD spectrum is shown in FIG. 12.

The Comparative Example was performed to reflect the prior art, in particular the teaching of CN 104709920 A. Said document relates to a process for the preparation of tin-containing molecular sieves. More specifically, said document discloses a process including the steps of (1) providing an aqueous mixture which comprises a boron source, a silicon source, and a structure directing agent, (2) heating the mixture up to 50° C., (3) adding a tin source to the mixture, and (4) subjecting the mixture to hydrothermal crystallization conditions (see example 1 in paragraphs [0035] to [0039] of CN 104709920 A). In contrast to the teaching of CN 104709920 A, in particular Example 1 of the present invention includes a pre-crystallization step under hydrothermal conditions leading to a different product. This finding was confirmed by X-ray analysis, as shown in the respective Figures herein.

SHORT DESCRIPTION OF THE FIGURES

FIG. 1 shows the UV-VIS spectrum of the zeolitic material prepared according to Example 1, determined as described in Reference Example 2. The x axis shows the wavelength in nm, with tick marks, from left to right, at 200; 300; 400; 500; 600. The y axis shows the K–M value, with tick marks, from bottom to top, at 0,0; 0,5; 1,0; 1,5; 2,0.

FIG. 2 shows an SEM picture of the zeolitic material prepared according to Example 1, determined as described in Reference Example 1. In the lower left hand corner, the scale is shown (75000:1). In the lower right hand corner, the black and white rule shows the dimension of 500 nm.

FIG. 3 shows the FT-IR spectrum of the zeolitic material prepared according to Example 1, determined as described in Reference Example 3. The x axis shows the wavenumbers in $cm^{-1}$, with tick marks, from left to right, at 4000; 3500; 3000; 2500; 2000; 1500. The y axis shows the extinction, with tick marks, from bottom to top, at 0,0; 0,1; 0,2; 0,3; 0,4; 0,5; 0,6; 0,7; 0,8; 0,9; 1.0.

FIG. 4 shows the UV-VIS spectrum of the zeolitic material prepared according to Example 2, determined as described in Reference Example 2. The x axis shows the wavelength in nm, with tick marks, from left to right, at 200; 300; 400; 500; 600. The y axis shows the K–M value, with tick marks, from bottom to top, at 0,0; 0,5; 1,0; 1,5; 2,0.

FIG. 5 shows an SEM picture of the zeolitic material prepared according to Example 2, determined as described in Reference Example 1. In the lower left hand corner, the scale is shown (75000:1). In the lower right hand corner, the black and white rule shows the dimension of 500 nm.

FIG. 6 shows the FT-IR spectrum of the zeolitic material prepared according to Example 2, determined as described in Reference Example 3. The x axis shows the wavenumbers in $cm^{-1}$, with tick marks, from left to right, at 4000; 3500; 3000; 2500; 2000; 1500. The y axis shows the extinction, with tick marks, from bottom to top, at −0,00; 0,05; 0,10; 0,15; 0,20; 0,25; 0,30; 0,35; 0,40; 0,45; 0,50; 0,55; 0,60; 0,65; 0,70.

FIG. 7 shows the UV-VIS spectrum of the zeolitic material prepared according to Example 3, determined as described in Reference Example 2. The x axis shows the wavelength in nm, with tick marks, from left to right, at 200; 300; 400; 500; 600. They axis shows the K-M value, with tick marks, from bottom to top, at 0,0; 0,5; 1,0; 1,5; 2,0.

FIG. 8 shows an SEM picture of the zeolitic material prepared according to Example 3, determined as described in Reference Example 1. In the lower left hand corner, the scale is shown (75000:1). In the lower right hand corner, the black and white rule shows the dimension of 500 nm.

FIG. 9 shows the FT-IR spectrum of the zeolitic material prepared according to Example 3, determined as described in Reference Example 3. The x axis shows the wavenumbers in $cm^{-1}$, with tick marks, from left to right, at 4000; 3500; 3000; 2500; 2000; 1500. The y axis shows the extinction, with tick marks, from bottom to top, at 0,00; 0,05; 0,10; 0,15; 0,20; 0,25; 0,30; 0,35; 0,40; 0,45; 0,50; 0,55; 0,60; 0,65; 0,70; 0,57; 0,80.

FIG. 10 shows the XRD spectrum of the zeolitic material prepared according to Example 1. The x axis shows the 2 theta angle in °, with tick marks, from left to right, at 2; 10; 20; 30; 40; 50; 60; 70. The y axis shows the lin counts, with tick marks, from bottom to top, at 0; 27370.

FIG. 11 shows the XRD spectrum of the zeolitic material prepared according to Example 3. The x axis shows the 2 theta angle in °, with tick marks, from left to right, at 2; 10; 20; 30; 40; 50; 60; 70. The y axis shows the lin counts, with tick marks, from bottom to top, at 0; 18249.

FIG. 12 shows the XRD spectrum of the material prepared according to Comparative Example 1. The x axis shows the 2 theta angle in °, with tick marks, from left to right, at 0; 10; 20; 30; 40; 50; 60. The y axis shows the intensity as impulse value, with tick marks, from bottom to top, at 0; 6000.

CITED LITERATURE

U.S. Pat. No. 9,108,190
J. Mater. Chem. A 2 (2014) pp 20252-20262
CN 104709920 A

The invention claimed is:

1. A tin-containing zeolitic material having framework type BEA, obtained by a process comprising
    (i.1) providing an aqueous synthesis mixture comprising a boron source, a silicon source, and a BEA structure directing agent;
    (i.2) subjecting the synthesis mixture provided in (i) to hydrothermal pre-crystallization conditions;
    (i.3) adding a tin source to the mixture obtained from (i.2);
    (i.4) subjecting the aqueous synthesis mixture obtained from (i.3) to hydrothermal crystallization conditions, obtaining a tin-containing zeolitic material having framework type BEA comprised in its mother liquor.

2. A process for preparing a tin-containing zeolitic material according to claim 1 having framework type BEA, comprising (i.1) providing an aqueous synthesis mixture comprising a boron source, a silicon source, and a BEA structure directing agent;
(i.2) subjecting the synthesis mixture provided in (i) to hydrothermal pre-crystallization conditions;
(i.3) adding the tin source to the mixture obtained from (i.2);
(ii) subjecting the aqueous synthesis mixture obtained from (i.3) to hydrothermal crystallization conditions, obtaining a tin-containing zeolitic material having framework type BEA comprised in its mother liquor.

3. The process of claim 2, wherein at least 99 weight-% of the aqueous synthesis mixture provided in (i.1) consist of water, the boron source, the silicon source, and the framework type BEA structure directing agent, and wherein at least 99 weight-% of the aqueous synthesis mixture subjected to hydrothermal crystallization conditions in (ii) consist of the mixture obtained from (i.3) and the tin source.

4. The process of claim 2, wherein the hydrothermal pre-crystallization conditions according to (i.2) comprise a hydrothermal pre-crystallization temperature in the range of from 100 to 200° C.

5. The process of claim 2, wherein the tin source is one or more of tin(II) alkoxides, tin(IV) alkoxides, tin(II) salts of organic acids, tin(IV) salts of organic acids, tin(II) salts of inorganic acids, tin(IV) salts of inorganic acids; wherein the boron source is one or more of boric acid, borates, boron halides, and boron oxide ($B_2O_3$); wherein the silicon source is one or more of fumed silica and colloidal silica; and wherein the framework type BEA structure directing agent comprises tetraethylammonium hydroxide.

6. The process of claim 2, wherein in the aqueous synthesis mixture provided in (i.1), the weight ratio of boron relative to silicon is in the range of from 0.4:1 to 2.0:1; the weight ratio of the framework type BEA structure directing agent relative to silicon is in the range of from 0.10:1 to 0.30:1; and wherein in the aqueous synthesis mixture provided in (i.3), the weight ratio of tin relative to silicon is in the range of from 0.005:1 to 0.1:1.

7. The process of claim 2, wherein the hydrothermal crystallization conditions according to (ii) comprise a hydrothermal crystallization temperature in the range of from 100 to 200° C.

8. The process of claim 2, further comprising
(iii) separating the tin-containing zeolitic material having framework type BEA from its mother liquor by washing the tin-containing zeolitic material having framework type BEA with a washing agent;
(iv) subjecting the tin-containing zeolitic material having framework type BEA obtained from (iii) to drying conditions, at a drying temperature in the range of from 60 to 200° C.;
(v) subjecting the tin-containing zeolitic material having framework type BEA obtained from (iv) to calcination conditions, at a calcination temperature in the range of from 400 to 700° C.

9. The process of claim 2, further comprising
(vi) subjecting the tin-containing zeolitic material having framework type BEA to deboronation, obtaining a deboronated tin-containing zeolitic material, said subjecting to deboronation comprising
(vi.1) treating the tin-containing zeolitic material having framework type BEA with an acid;
(vi.2) washing the acid-treated tin-containing zeolitic material having framework type BEA with a washing agent, preferably water;

or comprising
(vi.1) treating the tin-containing zeolitic material having framework type BEA with water which does not contain an acid;
(vi.2) optionally washing the water-treated tin-containing zeolitic material having framework type BEA with a washing agent, preferably water;
wherein the treating according to (vi.1) is carried out at a temperature of the aqueous mixture comprising the tin-containing zeolitic material having framework type BEA, in the range of from 60 to 100° C.

10. The process of claim 9, further comprising
(vii) subjecting the deboronated tin-containing zeolitic material having framework type BEA to drying conditions, at a drying temperature in the range of from 60 to 200° C.;
(viii) subjecting the deboronated tin-containing zeolitic material having framework type BEA obtained from (vii) to calcination conditions, at a calcination temperature in the range of from 400 to 700° C.

11. The process of claim 2, wherein at least 99.5 weight-% of the aqueous synthesis mixture provided in (i.1) consist of water, the boron source, the silicon source, and the framework type BEA structure directing agent, and wherein at least 99.5 weight-%, of the aqueous synthesis mixture subjected to hydrothermal crystallization conditions in (ii) consist of the mixture obtained from (i.3) and the tin source.

12. The process of claim 2, wherein at least 99.9 weight-% of the aqueous synthesis mixture provided in (i.1) consist of water, the boron source, the silicon source, and the framework type BEA structure directing agent, and wherein at 99.9 weight-% of the aqueous synthesis mixture subjected to hydrothermal crystallization conditions in (ii) consist of the mixture obtained from (i.3) and the tin source.

13. The process of claim 2, wherein the hydrothermal pre-crystallization conditions according to (i.2) comprise a hydrothermal pre-crystallization temperature in the range of from 110 to 190° C.

14. The process of claim 2, wherein the hydrothermal pre-crystallization conditions according to (i.2) comprise a hydrothermal pre-crystallization temperature in the range of from 120 to 180° C.

15. The process of claim 2, wherein the tin source is Sn(II)-acetate or Sn(IV)-tert-butoxide; wherein the boron source is boric acid; wherein the silicon source ammonia-stabilized colloidal silica; and wherein the framework type BEA structure directing agent is tetraethylammonium hydroxide.

16. A tin- and boron-containing zeolitic material having framework type BEA, having a tin content in the range of from 0.5 to 10 weight-%, calculated as elemental tin and based on the total weight of the tin- and boron-containing zeolitic material having framework type BEA, and having a boron content in the range of from 0. 5 to 9 weight-%, calculated as elemental boron and based on the total weight of the tin- and boron-containing zeolitic material having framework type BEA;
and having an XRD spectrum comprising peaks at 2 theta diffraction angles of $(8.0\pm0.1)°$, $(22.0\pm0.1)°$, $(23.0\pm0.1)°$, $(25.9\pm0.1)°$, $(27.3\pm0.1)°$.

17. The tin- and boron-containing zeolitic material having framework type BEA of claim 16, further characterized by one or more of the following features:
a BET specific surface of at least 400 m$^2$/g, as determined according to DIN 66131;
a crystallinity of at least 50%, as determined according to XRD;

a micropore volume in the range of from 0.12 to 0.14 cm³/g, as determined according to DIN 66135;

a mean crystal size of at most 100 nm, as determined according to SEM;

an absorption band with a maximum in the range of from 200 to 220 nm and optionally a further absorption band with a maximum in the range of from 230 to 300 nm, as determined according to UV-VIS;

an FT-IR spectrum wherein the ratio of the absorption maximum of a first band with a maximum in the range of from 3700 to 3750 cm$^{-1}$ relative to the absorption maximum of a second band with a maximum in the range of from 3550 to 3699 cm$^{-1}$ is in the range of from 0.5 to 2.0;

a water uptake of at least 10 weight-%, as determined via water adsorption-desorption isotherms.

18. A tin-containing zeolitic material having framework type BEA having a tin content in the range of from 0.5 to 10 weight %, calculated as elemental tin and based on the total weight of the tin-containing, zeolitic material having framework type BEA, and having a boron content in the range of from 0 to 0.15 weight-%, calculated as elemental boron and based on the total weight of the tin- and boron-containing zeolitic material having framework type BEA, wherein at least 99 weight-% of the zeolitic framework consist of Sn, B, Si, O, and H, having a crystallinity of at least 50%, as determined according to XRD, having a water uptake in the range of from 15 to 35 weight-%, as determined via water adsorption-desorption isotherms, and having an absorption band with a maximum in the range of from 200 to 220 nm and optionally a further absorption band with a maximum in the range of from 230 to 300 nm, as determined according to UV-VIS.

19. A catalytically active material comprising the tin- and boron-containing zeolitic material having framework type BEA according to claim 16.

20. A catalytically active material comprising the tin-containing zeolitic material having framework type BEA according to claim 18.

* * * * *